United States Patent
Park et al.

(10) Patent No.: US 10,495,104 B2
(45) Date of Patent: Dec. 3, 2019

(54) AIR CLEANER

(71) Applicant: LG ELECTRONICS INC., Seoul (KR)

(72) Inventors: Jaekyun Park, Seoul (KR); Hyunpil Ha, Seoul (KR); Soonki Jung, Seoul (KR); Yeongcheol Mun, Seoul (KR); Soohyun Bae, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 89 days.

(21) Appl. No.: 15/659,989

(22) Filed: Jul. 26, 2017

(65) Prior Publication Data

US 2017/0321715 A1    Nov. 9, 2017

Related U.S. Application Data

(63) Continuation of application No. 15/363,587, filed on Nov. 29, 2016.

(30) Foreign Application Priority Data

Feb. 26, 2016  (KR) ........................ 10-2016-0023663
Jun. 22, 2016  (KR) ........................ 10-2016-0077888
Oct. 25, 2016  (KR) ........................ 10-2016-0139376

(51) Int. Cl.
*B01D 46/00* (2006.01)
*F04D 29/40* (2006.01)
(Continued)

(52) U.S. Cl.
CPC .............. *F04D 29/403* (2013.01); *A61L 9/22* (2013.01); *B01D 46/002* (2013.01);
(Continued)

(58) Field of Classification Search
CPC ...... F04D 29/403; F04D 29/703; F24F 11/89; F24F 11/30; F24F 11/52; F24F 2013/205;
(Continued)

(56) References Cited

U.S. PATENT DOCUMENTS 4,210,429 A    7/1980   Golstein
4,365,980 A    12/1982  Culbert et al.
(Continued)

FOREIGN PATENT DOCUMENTS

CN    1487246    4/2004
CN    1510348    7/2004
(Continued)

OTHER PUBLICATIONS

European Search Report dated Jun. 21, 2017 issued in Application No. 16201093.8.
(Continued)

*Primary Examiner* — T. Bennett McKenzie
(74) *Attorney, Agent, or Firm* — Ked & Associates LLP

(57) ABSTRACT

An air flow controller for an air cleaner and an air cleaner are provided. The air flow controller may include a fan, and a housing, the fan being provided in the housing and the housing being movable from an initial horizontal position in which the air flow controller directs air flow in a vertical direction to an inclined position in which the air flow controller directs air flow in a diagonal direction.

20 Claims, 24 Drawing Sheets

(51) Int. Cl.

| | | |
|---|---|---|
| *F24F 11/89* | (2018.01) | |
| *F24F 13/12* | (2006.01) | |
| *F24F 13/14* | (2006.01) | |
| *F24F 3/16* | (2006.01) | |
| *F04D 29/70* | (2006.01) | |
| *F24F 7/007* | (2006.01) | |
| *F24F 13/10* | (2006.01) | |
| *F24F 13/20* | (2006.01) | |
| *F24F 13/28* | (2006.01) | |
| *B01D 46/24* | (2006.01) | |
| *A61L 9/22* | (2006.01) | |
| *F24F 11/30* | (2018.01) | |
| *F24F 1/0071* | (2019.01) | |
| *F24F 110/64* | (2018.01) | |
| *F24F 11/52* | (2018.01) | |

(52) U.S. Cl.
CPC ..... *B01D 46/0008* (2013.01); *B01D 46/0047* (2013.01); *B01D 46/2403* (2013.01); *F04D 29/703* (2013.01); *F24F 1/0071* (2019.02); *F24F 3/16* (2013.01); *F24F 7/007* (2013.01); *F24F 11/30* (2018.01); *F24F 11/89* (2018.01); *F24F 13/10* (2013.01); *F24F 13/12* (2013.01); *F24F 13/14* (2013.01); *F24F 13/20* (2013.01); *F24F 13/28* (2013.01); *A61L 2209/11* (2013.01); *A61L 2209/12* (2013.01); *A61L 2209/14* (2013.01); *B01D 2273/30* (2013.01); *F24F 11/52* (2018.01); *F24F 2013/205* (2013.01); *F24F 2110/64* (2018.01)

(58) Field of Classification Search
CPC .. F24F 1/0071; F24F 3/16; F24F 7/007; F24F 13/10; F24F 13/12; F24F 13/14; F24F 13/20; F24F 13/28; A61L 2209/11; A61L 2209/12; A61L 2209/14; A61L 9/22; B01D 2273/30; B01D 46/00; B01D 46/0008; B01D 46/002; B01D 46/0047; B01D 46/2403
USPC ......................................................... 55/467
See application file for complete search history.

(56) References Cited

U.S. PATENT DOCUMENTS

| | | | |
|---|---|---|---|
| 4,905,340 A | 3/1990 | Gutschmit | |
| 5,117,652 A | 6/1992 | Takeuchi et al. | |
| 5,264,015 A | 11/1993 | Matsui | |
| 5,334,248 A | 8/1994 | Kwak | |
| 5,641,343 A | 6/1997 | Frey | |
| 5,753,000 A | 5/1998 | Chiu et al. | |
| 5,837,020 A | 11/1998 | Cartellone | |
| 6,053,968 A | 4/2000 | Miller | |
| 6,264,712 B1 | 7/2001 | Decker | |
| 6,280,493 B1 | 8/2001 | Eubank | |
| 6,494,940 B1 | 12/2002 | Hak | |
| 6,680,028 B1 | 1/2004 | Harris | |
| 6,955,708 B1 | 10/2005 | Julos et al. | |
| 8,212,146 B1 | 7/2012 | Moore | |
| 9,821,259 B2 | 11/2017 | Bae et al. | |
| 9,943,794 B2 | 4/2018 | Jung | |
| 9,950,289 B2 | 4/2018 | Jung | |
| 2002/0157415 A1 | 10/2002 | Liu | |
| 2004/0144249 A1 | 7/2004 | Kang et al. | |
| 2005/0066634 A1 | 3/2005 | Genn et al. | |
| 2006/0107834 A1 | 5/2006 | Vandenbelt et al. | |
| 2006/0201119 A1 | 9/2006 | Song | |
| 2006/0277875 A1 | 12/2006 | Schuld | |
| 2007/0137489 A1 | 6/2007 | Luo | |
| 2007/0221061 A1 | 9/2007 | Steiner et al. | |
| 2008/0286163 A1 | 11/2008 | Garfield | |
| 2010/0225012 A1 | 9/2010 | Fitton et al. | |
| 2010/0225015 A1 | 9/2010 | Techlin et al. | |
| 2011/0033346 A1 | 2/2011 | Bohlen | |
| 2011/0308210 A1 | 12/2011 | Crabtree et al. | |
| 2013/0055692 A1 | 3/2013 | Cecchi et al. | |
| 2013/0090052 A1 | 4/2013 | Akhtar | |
| 2014/0020561 A1 | 1/2014 | Aery | |
| 2014/0102664 A1 | 4/2014 | Kim et al. | |
| 2014/0216251 A1 | 8/2014 | Jun et al. | |
| 2014/0216259 A1 | 8/2014 | Iwaki | |
| 2015/0273376 A1 | 10/2015 | Sohn et al. | |
| 2015/0306533 A1 | 10/2015 | Matlin et al. | |
| 2015/0345816 A1 | 12/2015 | Donovan | |
| 2016/0032942 A1 | 2/2016 | Jung et al. | |
| 2016/0184753 A1 | 6/2016 | Chu et al. | |

FOREIGN PATENT DOCUMENTS

| | | |
|---|---|---|
| CN | 1598413 | 3/2005 |
| CN | 1619229 | 5/2005 |
| CN | 1752617 | 3/2006 |
| CN | 2769724 | 4/2006 |
| CN | 1784258 | 6/2006 |
| CN | 101021345 | 8/2007 |
| CN | 101105307 | 1/2008 |
| CN | 201106913 | 8/2008 |
| CN | 201482362 | 5/2010 |
| CN | 102748817 | 10/2012 |
| CN | 202568987 | 12/2012 |
| CN | 103574770 | 2/2014 |
| CN | 103673076 | 3/2014 |
| CN | 103712318 | 4/2014 |
| CN | 103727632 | 4/2014 |
| CN | 203518040 | 4/2014 |
| CN | 103930730 | 7/2014 |
| CN | 103982994 | 8/2014 |
| CN | 203893332 | 10/2014 |
| CN | 203964288 | 11/2014 |
| CN | 102661295 | 12/2014 |
| CN | 204084651 | 1/2015 |
| CN | 104329785 | 2/2015 |
| CN | 204141826 | 2/2015 |
| CN | 104406235 | 3/2015 |
| CN | 104456772 | 3/2015 |
| CN | 104603545 | 5/2015 |
| CN | 204447560 | 7/2015 |
| CN | 104937359 | 9/2015 |
| CN | 104971567 | 10/2015 |
| CN | 104990155 | 10/2015 |
| CN | 105091106 | 11/2015 |
| CN | 105185242 | 12/2015 |
| CN | 105221452 | 1/2016 |
| CN | 204933080 | 1/2016 |
| CN | 204963008 | 1/2016 |
| CN | 105299862 | 2/2016 |
| CN | 105299863 | 2/2016 |
| CN | 105333499 | 2/2016 |
| CN | 105333528 | 2/2016 |
| CN | 206300285 | 7/2017 |
| CN | 206300287 | 7/2017 |
| CN | 206300288 | 7/2017 |
| CN | 206338921 | 7/2017 |
| DE | 9312051 | 10/1993 |
| EP | 1 950 500 | 7/2008 |
| EP | 2 072 920 | 6/2009 |
| EP | 2 476 968 | 7/2012 |
| EP | 2 837 897 | 2/2015 |
| EP | 2 853 835 | 4/2015 |
| GB | 995962 | 6/1965 |
| GB | 996962 | 6/1965 |
| GB | 2 345 005 | 6/2000 |
| GB | 2516058 | 1/2015 |
| JP | H 04-103549 | 9/1992 |
| JP | H 06-50180 | 6/1994 |
| JP | 7-208779 | 8/1995 |
| JP | 2000-354724 | 12/2000 |
| JP | 2006-022977 | 1/2006 |
| JP | 2007-105578 | 4/2007 |
| JP | 4526372 | 8/2010 |

(56) References Cited

FOREIGN PATENT DOCUMENTS

| | | | | |
|---|---|---|---|---|
| JP | 2012-120720 | 6/2012 | | |
| JP | 2013-217580 | 10/2013 | | |
| JP | 2014-507277 | 3/2014 | | |
| JP | 2014-119224 | 6/2014 | | |
| JP | 2015-080737 | 4/2015 | | |
| JP | 2015-108497 | 6/2015 | | |
| JP | 5740503 | 6/2015 | | |
| JP | 2015-120138 | 7/2015 | | |
| JP | 5800652 | 10/2015 | | |
| JP | 2016-034602 | 3/2016 | | |
| KR | 20-1993-0002444 | 5/1993 | | |
| KR | 10-0139487 | 6/1998 | | |
| KR | 20-0173274 | 3/2000 | | |
| KR | 20-0289687 | 9/2002 | | |
| KR | 20-0342073 | 2/2004 | | |
| KR | 10-2004-0056151 | 6/2004 | | |
| KR | 10-2004-0108462 | 12/2004 | | |
| KR | 10-0508312 | 8/2005 | | |
| KR | 10-2005-0110233 | 11/2005 | | |
| KR | 10-2005-0115343 | 12/2005 | | |
| KR | 10-2006-0023457 | 3/2006 | | |
| KR | 10-2006-0026319 | 3/2006 | | |
| KR | 10-0674271 | 1/2007 | | |
| KR | 20-2008-0001777 | 6/2008 | | |
| KR | 10-2009-0058446 | 6/2009 | | |
| KR | 10-2009-0087652 | 8/2009 | | |
| KR | 10-2010-0056797 | 5/2010 | | |
| KR | 10-2010-0062121 | 6/2010 | | |
| KR | 10-2010-0070069 | 6/2010 | | |
| KR | 10-2010-0102507 | 9/2010 | | |
| KR | 10-2011-0029870 | 3/2011 | | |
| KR | 10-2012-0060279 | 6/2012 | | |
| KR | 10-2012-0071992 | 7/2012 | | |
| KR | 10-1168738 | 7/2012 | | |
| KR | 10-1203570 | 11/2012 | | |
| KR | 10-2012-0136137 | 12/2012 | | |
| KR | 10-2013-0036447 | 4/2013 | | |
| KR | 10-1278334 | 6/2013 | | |
| KR | 10-1342606 | 12/2013 | | |
| KR | 10-2014-0039703 | 4/2014 | | |
| KR | 10-1385290 | 4/2014 | | |
| KR | 10-2014-0092953 | 7/2014 | | |
| KR | 10-2014-0094414 | 7/2014 | | |
| KR | 10-2014-0096971 | 8/2014 | | |
| KR | 10-2015-0005594 | 1/2015 | | |
| KR | 10-1500501 | 3/2015 | | |
| KR | 10-1506653 | 3/2015 | | |
| KR | 10-1512664 | 4/2015 | | |
| KR | 10-1516365 | 5/2015 | | |
| KR | 10-2016-0012796 | 2/2016 | | |
| KR | 10-2016-0015084 | 2/2016 | | |
| KR | 10-2016-0017587 | 2/2016 | | |
| KR | 1020160012796 | * | 2/2016 | ............ B01D 46/00 |
| KR | 10-2016-0028292 | 3/2016 | | |
| KR | 10-1599634 | 3/2016 | | |
| KR | 10-2016-0048499 | 5/2016 | | |
| KR | 10-2016-0053649 | 5/2016 | | |
| KR | 10-2016-0104837 | 9/2016 | | |
| WO | WO 2010/109944 | 9/2010 | | |
| WO | WO 2013/121672 | 8/2013 | | |
| WO | WO 2015/171 | 11/2015 | | |

OTHER PUBLICATIONS

Korean Office Action dated Jun. 21, 2017 issued in Application No. 10-2017-0056789.
Korean Office Action dated Jun. 21, 2017 issued in Application No. 10-2017-0056790.
Korean Office Action dated Jun. 21, 2017 issued in Application No. 10-2017-0056791.
European Search Report dated Jun. 23, 2017 issued in Application No. 16201089.6.
European Search Report dated Jun. 23, 2017 issued in Application No. 16201088.8.
Korean Office Action dated Jun. 30, 2017 issued in Application No. 10-2017-0056864.
European Search Report dated Jul. 14, 2017 issued in Application No. 16201094.6.
European Search Report dated Jul. 20, 2017 issued in Application No. 16201091.2.
Korean Notice of Allowance dated Aug. 15, 2017 issued in Application No. 10-2016-0074369.
Korean Office Action dated Aug. 22, 2017 issued in Application No. 10-2016-0073055.
United States Office Action dated Oct. 24, 2018 issued in co-pending related U.S. Appl. No. 15/363,643.
United States Office Action dated Oct. 25, 2018 issued in co-pending related U.S. Appl. No. 15/441,957.
Chinese Office Action dated Mar. 5, 2019 issued in Application No. 201611089126.6 (with English Translation).
Chinese Office Action dated Mar. 27, 2019 issued in Application No. 201611089196.1 (with English Translation).
Korean Office Action dated May 2, 2019 issued in Application No. 10-2019-0025204.
United States Office Action dated Mar. 1, 2019 issued in co-pending related U.S. Appl. No. 15/363,438.
United States Office Action dated Mar. 5, 2019 issued in co-pending related U.S. Appl. No. 15/363,587.
European Search Report dated Jul. 20, 2017 issued in Application No. 16201090.4
Korean Office Action dated Aug. 31, 2017 issued in Application No. 10-2016-0073090.
United States Office Action dated Jan. 20, 2017 issued in U.S. Appl. No. 15/363,156.
United States Office Action dated Jan. 20, 2017 issued in U.S. Appl. No. 15/364,369.
United States Office Action dated Jan. 23, 2017 issued in U.S. Appl. No. 15/363,204.
United States Office Action dated Jan. 23, 2017 issued in U.S. Appl. No. 15/364,410.
United States Office Action dated Jan. 23, 2017 issued in U.S. Appl. No. 15/364,467.
Korean Office Action dated Jan. 26, 2017 issued in Application No. 10-2016-0073055.
Korean Office Action dated Jan. 26, 2017 issued in Application No. 10-2016-0073083.
Korean Office Action dated Jan. 26, 2017 issued in Application No. 10-2016-0077888.
United States Office Action dated Feb. 10, 2017 issued in U.S. Appl. No. 15/363,111.
International Search Report dated Mar. 20, 2017 issued in Application No. PCT/KR2016/013906.
International Search Report dated Mar. 21, 2017 issued in Application No. PCT/KR2016/013907.
International Search Report dated Mar. 30, 2017 issued in Application No. PCT/KR2016/013912.
International Search Report dated Mar. 30, 2017 issued in Application No. PCT/KR2016/013908.
Korean Office Action dated Apr. 20, 2017 issued in Application No. 10-2016-0132790.
European Search Report dated Apr. 25, 2017 issued in Application No. 16201086.2-1602.
European Search Report dated Apr. 25, 2017 issued in Application No. 17157045.0-1602.
European Search Report dated Jun. 21, 2017 issued in Application No. 16201095.3.
Korean Office Action dated Jun. 21, 2017 issued in Application No. 10-2017-0056865.
Korean Office Action dated Jun. 21, 2017 issued in Application No. 10-2017-0056885.
Korean Office Action dated Jun. 21, 2017 issued in Application No. 10-2017-0056886.
U.S. Office Action issued in U.S. Appl. No. 15/364,369 dated Jul. 14, 2017.
United States Office Action dated Nov. 8, 2018 issued in co-pending related U.S. Appl. No. 15/363,438.
European Search Report dated Jan. 17, 2018.

(56) References Cited

OTHER PUBLICATIONS

European Search Report dated Jan. 18, 2018.
United States Office Action dated Dec. 3, 2018 issued in co-pending related U.S. Appl. No. 15/363,587.
United States Office Action dated Feb. 6, 2019 issued in co-pending related U.S. Appl. No. 15/660,105.
United States Office Action dated Feb. 6, 2019 issued in co-pending related U.S. Appl. No. 15/660,122.
United States Office Action dated Feb. 21, 2019 issued in co-pending related U.S. Appl. No. 15/659,878.
Chinese Office Action dated Feb. 22, 2019 with English Translation.
U.S. Office Action issued in U.S. Appl. No. 15/660,076 dated May 8, 2019.
Chinese Office Action dated Jan. 11, 2019 issued in Application No. 201611089233.9 (with English Translation).
Korean Office Action dated Apr. 12, 2018.
Korean Notice of Allowance dated Apr. 17, 2018.
Korean Notice of Allowance dated Jun. 11, 2018.
European Search Report dated Jul. 14, 2017 issued in Application No. 16201092.0.
Korean Office Action dated Aug. 31, 2017 issued in Application No. 10-2016-0073063.
Chinese Office Action dated Feb. 28, 2019 issued in Application No. 201611087595.4 (with English Translation).
Chinese Office Action dated Feb. 28, 2019 issued in Application No. 201611089358.1 (with English Translation).
Korean Office Action dated Oct. 31, 2017.
U.S. Appl. No. 15/363,438, filed Nov. 29, 2016.
U.S. Appl. No. 15/363,587, filed Nov. 29, 2016.
U.S. Appl. No. 15/363,643, filed Nov. 29, 2016.
U.S. Appl. No. 15/441,957, filed Feb. 24, 2017.
U.S. Appl. No. 15/659,869, filed Jul. 26, 2017.
U.S. Appl. No. 15/659,878, filed Jul. 26, 2017.
U.S. Appl. No. 15/660,105, filed Jul. 26, 2017.
U.S. Appl. No. 15/660,122, filed Jul. 26, 2017.
U.S. Appl. No. 15/660,076, filed Jul. 26, 2017.
U.S. Appl. No. 15/660,207, filed Jul. 26, 2017.
U.S. Appl. No. 15/660,287, filed Jul. 26, 2017.
U.S. Appl. No. 15/660,362, filed Jul. 26, 2017.
U.S. Appl. No. 15/660,462, filed Jul. 26, 2017.
U.S. Appl. No. 15/926,129, filed Mar. 20, 2018.
U.S. Appl. No. 16/409,017, filed May 10, 2019.
U.S. Appl. No. 15/363,111, filed Nov. 29, 2016.
U.S. Appl. No. 15/363,156, filed Nov. 29, 2016.
U.S. Appl. No. 15/363,204, filed Nov. 29, 2016.
U.S. Appl. No. 15/364,467, filed Nov. 30, 2016.
U.S. Appl. No. 15/364,369, filed Nov. 30, 2016.
U.S. Appl. No. 15/364,410, filed Nov. 30, 2016.
U.S. Appl. No. 15/363,587, filed Nov. 29, 2016, Thomas B. Mckenzie.
U.S. Office Action issued in U.S. Appl. No. 15/660,287 dated Aug. 16, 2019.
United States Office Action dated Aug. 22, 2019 issued in co-pending related U.S. Appl. No. 15/926,129.
U.S. Office Action issued in U.S. Appl. No. 15/660,462 dated Jul. 19, 2019.
U.S. Office Action issued in U.S. Appl. No. 15/660,207 dated Jul. 22, 2019.
U.S. Appl. No. 15/659,869, Jul. 26, 2017, Robert Arthur Clemente.
Chinese Office Action dated May 27, 2019 issued in Application No. 201710637948.1 with English Translation.
Chinese Office Action dated Jun. 4, 2019 issued in Application No. 201710638173.X with English Translation.
Chinese Office Action dated Jun. 24, 2019 issued in Application No. 201710637920.8 with English Translation.
Chinese Office Action dated Jun. 26, 2019 issued in Application No. 201710790121.4 with English Translation.
Chinese Office Action dated Jun. 27, 2019 issued in Application No. 201710637967.4 with English Translation.
Chinese Office Action dated Jul. 16, 2019 issued in Application No. 201710638026.2. With English Translation.
Korean Notice of Allowance dated Jul. 1, 2019 issued in Application No. 10-2019-0063475.
U.S. Appl. No. 15/926,129, filed Mar. 20, 2018, Robert Arthur Clemente.
U.S. Appl. No. 15/659,869, filed Jul. 26, 2017, Robert Arthur Clemente.
U.S. Appl. No. 15/659,878, filed Jul. 26, 2017, Robert Arthur Clemente.
U.S. Appl. No. 15/660,105, filed Jul. 26, 2017, Robert Arthur Clemente.
U.S. Appl. No. 15/660,122, filed Jul. 26, 2017, Robert Arthur Clemente.
U.S. Appl. No. 15/363,438, filed Nov. 29, 2016, Thomas B. Mckenzie.
U.S. Appl. No. 15/659,989, filed Jul. 26, 2017, Duane Smith.
U.S. Appl. No. 15/660,076, filed Jul. 26, 2017, Duane Smith.
U.S. Appl. No. 15/660,207, filed Jul. 26, 2017, Duane Smith.
U.S. Appl. No. 15/660,287, filed Jul. 26, 2017, Duane Smith.
U.S. Appl. No. 15/660,362, filed Jul. 26, 2017, Duane Smith.
U.S. Appl. No. 15/660,462, filed Jul. 26, 2017, Duane Smith.
U.S. Appl. No. 15/363,643, filed Nov. 29, 2016, Thomas B. Mckenzie.
U.S. Appl. No. 16/409,017, filed May 10, 2019, Minh Chau Thi Pham.
Chinese Office Action dated Jun. 10, 2019 issued in Application No. 201710660027.7.
Chinese Office Action dated Jul. 29, 2019 issued in Application No. 201710659929.9.
Korean Office Action dated Jul. 22, 2019 issued in KR Application No. 10-2019-0060135.

* cited by examiner

AIR CLEANER

CROSS-REFERENCE TO RELATED APPLICATION(S)

This application is a Continuation application of prior U.S. patent application Ser. No. 15/363,587 filed Nov. 29, 2016, which claims priority under 35 U.S.C. 119 and 35 U.S.C. 365 to Korean Patent Application No. 10-2016-0077888 filed in Korea on Jun. 22, 2016, No. 10-2016-0023663 filed in Korea on Feb. 26, 2016, and No. 10-2016-0139376 filed in Korea on Oct. 25, 2016, which are hereby incorporated by reference in their entirety.

BACKGROUND

1. Field

An air cleaner is disclosed herein.

2. Background

An air cleaner is a device that suctions in and purifies contaminated air and then discharges purified air. For example, the air cleaner may include a blower that introduces outside air into the air cleaner and a filter capable of filtering dust and bacteria, for example.

Generally, the air cleaner is configured to purify an indoor space, such as a home or an office. According to the air cleaner in the related art, there is a problem that a capacity thereof is limited, and thus, purification of air in an entire indoor space is limited. Accordingly, air around the air cleaner is purified whereas air in a space away from the air cleaner is not purified.

In order to solve this problem, there are efforts to improve a performance of a fan provided in the air cleaner. However, noise generated by the fan gradually increases as a blowing amount of the fan increases. Accordingly, there is a problem is that reliability of the product is decreased. Finally, there is inconvenience that the air cleaner has to be moved by a user in order to purify air in the desired space.

A related art air cleaner is disclosed in Korean Publication No. KR10-2012-0071992 published on Jul. 3, 2012 and entitled AIR CLEANER, which is hereby incorporated by reference. According to this disclosure, air cleaning components, such as the fan and a filter are installed, in an inside of a case having a substantially rectangular parallelepiped shape of a main body of the air cleaner. Air suction ports are formed on a side portion and a lower portion of the main body of the air cleaner and an air discharge port is formed on an upper portion of the main body thereof.

According to this configuration, there is a problem in that a suction capacity is reduced as the contaminated air is suctioned from a limited direction, that is, from a side direction and a lower direction relative to the air cleaner. A corner portion of the case having a rectangular parallelepiped shape provides structural resistance interfering with the suction of air.

In addition, there is a problem that an air cleaning function is limited as purified air does not flow to a space away from the air cleaner, whereas air around the air cleaner is purified. That is, the air which is purified in the air cleaner is discharged in only one direction, that is, only in an upward direction. Further, there is a problem that a blowing capacity is limited as only one blowing fan is provided in the main body of the air cleaner.

BRIEF DESCRIPTION OF THE DRAWINGS

Embodiments will be described in detail with reference to the following drawings in which like reference numerals refer to like elements, and wherein.

DETAILED DESCRIPTION

Figure 1:
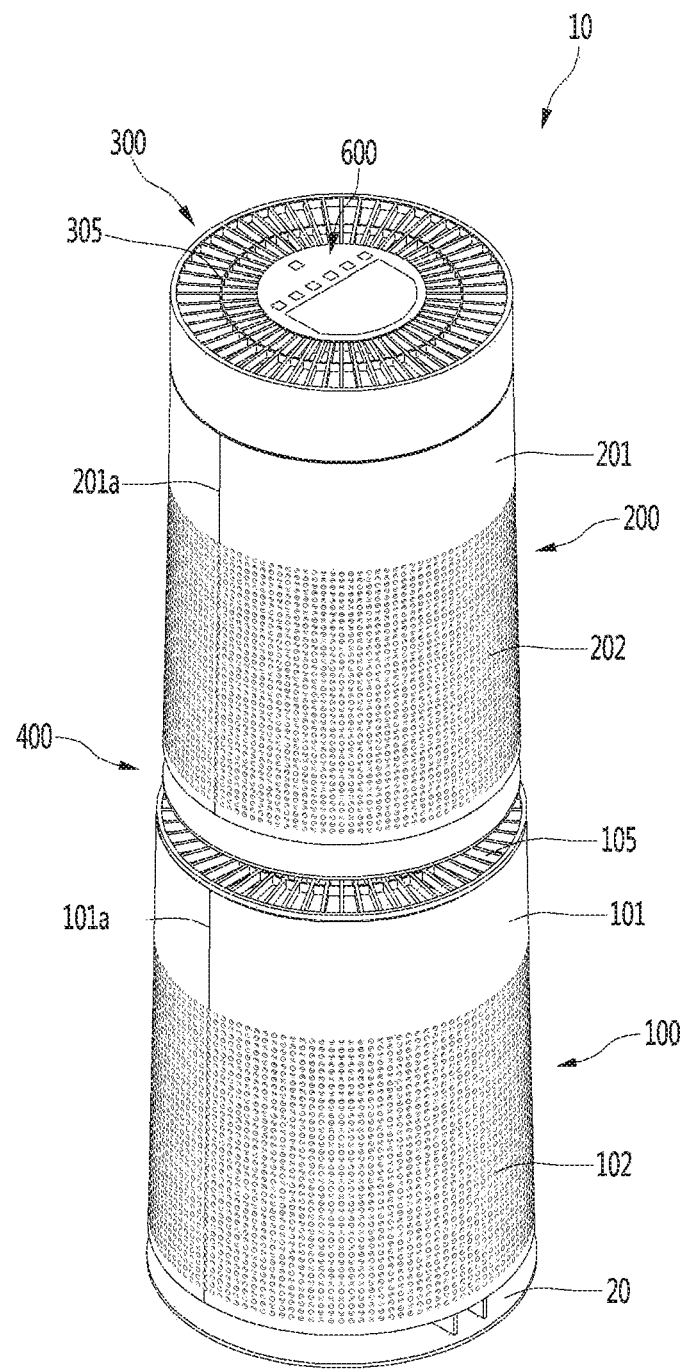
FIG. 1 is a perspective view of an air cleaner according to an embodiment.

Hereinafter, embodiments will be described in detail with reference to the illustrative drawings. Regarding the reference numerals assigned to the components in the drawings, it should be noted that the same components may be designated by the same reference numerals, wherever possible, even though they are shown in different drawings. Also, in the description of embodiments, specific description of known related configuration or functions may be omitted when it is deemed that such description may cause ambiguous interpretation of the present invention.

Also, in the description of embodiments, terms such as first, second, A, B, (a), (b) or the like may be used herein when describing components. Each of these terminologies is not used to define an essence, order or sequence of a corresponding component but used merely to distinguish the corresponding component from other component(s). In a case where it is described that any component is "connected" or "coupled" to another component, the component may be directly or indirectly connected or coupled to another component. However, it is to be understood that another component may be "connected" or "coupled" between the components.

Also, in the description of embodiments, terms such as first, second, A, B, (a), (b) or the like may be used herein when describing components. Each of these terminologies is not used to define an essence, order or sequence of a corresponding component but used merely to distinguish the corresponding component from other component(s). In a case where it is described that any component is "connected" or "coupled" to another component, the component may be directly or indirectly connected or coupled to another component. However, it is to be understood that another component may be "connected" or "coupled" between the components.

FIG. 1 is a perspective view of an air cleaner according to an embodiment. With reference to FIG. 1, the air cleaner 10 according to this embodiment may include blowing devices or blowers 100 and 200 that generate air flow and a flow adjusting device or adjuster 300 that adjusts a discharge direction of the air flow generated in the blowing devices 100 and 200. The blowing devices 100 and 200 may include a first blowing device 100 that generates a first air flow and a second blowing device 200 that generates a second air flow.

The first blowing device 100 and the second blowing device 200 may be provided in a vertical direction. For example, the second blowing device 200 may be provided on or at an upper side of the first blowing device 100. In this case, the first air flow is a flow of indoor air suctioned from a lower side of the air cleaner 10 and the second air flow is a flow of indoor air suctioned from an upper side of the air cleaner 10.

The air cleaner 10 may include cases 101 and 201 that form an outer appearance thereof. That is, the cases 101 and 201 may include a first case 101 that forms an outer appearance of the first blowing device 100. The first case 101 may have a cylindrical shape. An upper portion of the first case 101 may have a diameter which is less than a diameter of a lower portion thereof. That is, the first case 101 may have a truncated cone shape.

The first blowing device 100 and the second blowing device 200 may be referred to as a "first air cleaning module or cleaner 100" and a "second air cleaning module or cleaner 200", respectively, in that the first blowing device 100 and the second blowing device 200 perform a function of cleaning air in a space to be cleaned. The first blowing device 100 may be referred to as a "lower air cleaning module or cleaner" or "lower module or cleaner" in that the first blowing device 100 is provided at a lower portion of the air cleaner 10 and the second blowing device 200 may be referred to as an "upper air cleaning module or cleaner" or "upper module or cleaner" in that the second blowing device 200 is provided at an upper portion of the air cleaner 10. The flow adjusting device 300 may be referred to as "flow adjusting module or adjuster 300" or "flow control module 300".

The first case 101 may include a first separation portion 101a at which two parts which constitute the first case 101 may be assembled or disassembled. The first case 101 may further include a hinge portion or hinge which is provided on an opposite of the first separation portion 101a. The two parts may be capable of being relatively rotated about the hinge portion.

When at least any one part of the two parts rotates, the first case 101 may be opened and separated from the air cleaner 10. A locking device or lock may be provided at a portion at which the two parts are coupled, that is, a side opposite to the hinge portion. The locking device may include a locking projection or a magnet member or magnet. Components of the first blowing device 100 may be replaced or repaired by opening the first case 101.

The first case 101 may include a first suction portion or inlet 102 through which air may be suctioned in a radial direction. The first suction portion 102 may include one or more through hole formed to pass through at least a portion of the first case 101. A plurality of first suction portions 102 may be provided.

The plurality of first suction portions 102 may be evenly provided in a circumferential direction along an outer circumferential surface of the first case 101 so that air suction may be performed in any direction relative to the first case 101. That is, air may be suctioned in 360 degree directions relative to a center line that extends in the vertical direction and passes through an inside center of the first case 101.

Accordingly, a suction amount of air may be increased by the first case 101 having a cylindrical shape and the plurality of first suction portions 102 formed along the outer circumferential surface of the first case 101. Flow resistance to suctioned air may be reduced by avoiding a cube shape having edges or edge portions such as the case of the related art air cleaner.

Air which is suctioned in through the first suction portion 102 may flow substantially in the radial direction from the outer circumferential surface of the first case 101. Directions may be defined as follows. Referring to the FIG. 1, the vertical direction may refer to an axial direction and a transverse direction may refer to the radial direction. The axial direction may correspond to a central axis direction of the first fan 160 and the second fan 260, which are described hereinafter, that is, a motor shaft direction of the fan. The radial direction may refer to a direction which is perpendicular to the axial direction. The circumferential direction may refer to a virtual circle direction which is formed when rotating about the axial direction and having a distance of the radial direction as a rotational radius.

The first blowing device 100 may include a base 20 provided at a lower side of the first case 101 and placed on the ground. The base 20 may be positioned spaced apart from a lower end portion or end of the first case 101 in a downward direction. A base suction portion or inlet 103 may be formed in a space between the first case 101 and the base 20.

Air which is suctioned in through the base suction portion 103 may flow in an upward direction through a suction port 112 of a suction grill 110 (see FIG. 2), which may be provided in or at an upper side of the base 20. That is, the first blowing device 100 may include the plurality of suction portions 102 and the base suction portion 103. Air in a lower portion of the indoor space may be easily introduced to the first blowing device 100 through the plurality of suction portions 102 and the base suction portion 103. Accordingly, the suction amount of air may be increased.

A first discharge portion or outlet 105 may be formed at an upper portion of the first blowing device 100. The first discharge portion 105 may be formed on a first discharge grill 195 of a first discharge guide device or guide 190 (see, FIG. 8) which may be provided in the first blowing device 100. The first discharge guide 190 may form an outer appearance of an upper end portion or end of the first blowing device 100. Air discharged through the first discharge portion 105 may flow to the upper side in the axial direction.

The cases 101 and 201 may include a second case 201 which may form an outer appearance of the second blowing device 200. The second case 201 may have a cylindrical shape. An upper portion of the second case 201 may have a diameter which is less than a diameter of a lower portion thereof. That is, the second case 201 may have a truncated cone shape.

The second case 201 may include two parts and a hinge portion or hinge which are capable of being assembled or being disassembled through a second separation portion 201a. The second case 201 may be openable similar to the first case 101. The second case 201 may be the same or similar to the first case 101, and thus, repetitive disclosure has been omitted. Inner components of the second blowing device 200 may be replaced or repaired by opening the second case 201.

A diameter of a lower end portion of the second case 201 may be less than a diameter of the upper end portion or end of the first case 101. Accordingly, in a general shape of the cases 101 and 201, a lower cross-sectional area of the cases 101 and 102 may be formed to be greater than an upper cross-sectional area. Accordingly, the air cleaner 10 may be stably supported on the ground.

The second case 201 may include a second suction portion or inlet 202 through which air may be suctioned in the radial direction. The second suction portion 202 may include one or more through hole formed to pass through at least a portion of the second case 201. A plurality of the second suction portion 202 may be provided.

The plurality of second suction portions 202 may be evenly provided in the circumferential direction along an outer circumferential surface of the second case 201 so that air suction may be performed in any direction relative to the second case 201. That is, air may be suctioned in 360 degree directions relative to a center line that extends in the vertical direction and passes through an inside center of the second case 201.

Accordingly, a suction amount of air may be increased by the second case 201 having a cylindrical shape and the plurality of second suction portions 202 formed along the outer circumferential surface of the second case 201. Flow resistance to suctioned air may be reduced by avoiding a cube shape having an edge portions such as the case of the related are air cleaner. Air which is suctioned in through the second suction portion 202 may flow substantially in the radial direction from the outer circumferential surface of the second case 201.

The air cleaner 10 may include a dividing device or divider 400 provided between the first blowing device 100 and the second blowing device 200. By the dividing device 400, the second blowing device 200 may be positioned at the upper side of the first blowing device 100 spaced apart therefrom. The dividing device 400 will be described hereinafter, with reference to the drawings.

The flow adjusting device 300 may be provided at an upper side of the second blowing device 100. An air flow path of the second blowing device 100 may communicate with an air flow path of the flow adjusting device 300. The air passing through the second blowing device 100 may be discharged through a second discharge portion or outlet 305 to the outside via the air flow path of the flow adjusting device 300. The second discharge portion 305 may be provided on or at an upper end portion of the flow adjusting device 300.

Figure 18:
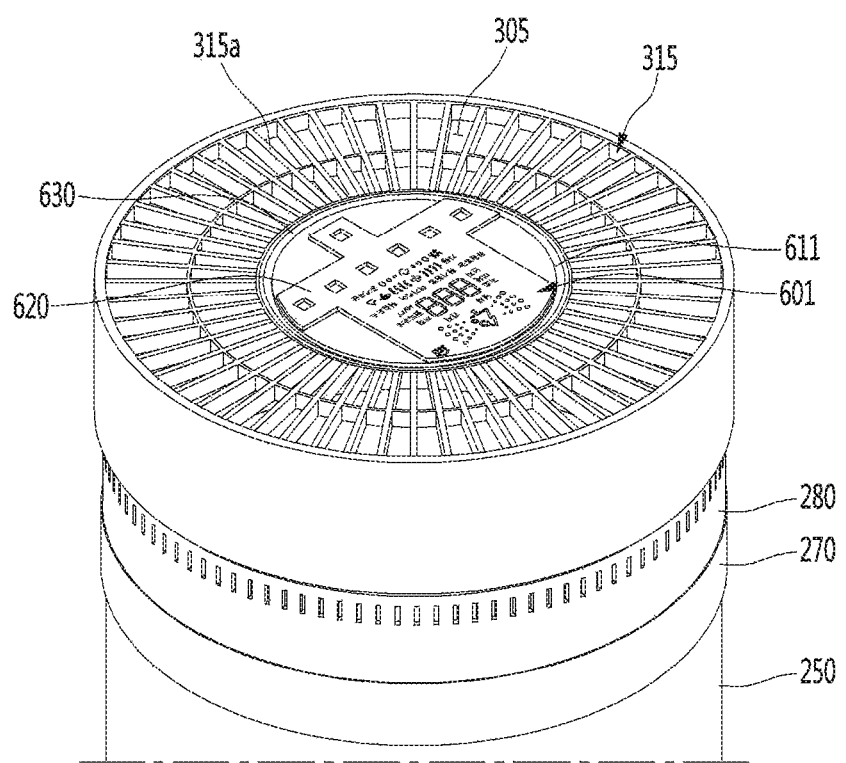
FIG. 18 is a view illustrating a state in which a printed circuit board (PCB) assembly is coupled to the discharge grill according to an embodiment.

The flow adjusting device 300 may be movable. That is, the flow adjusting device 300 may be movable between a laid-out state (first position), as illustrated in FIG. 1, or an inclined erected state (second position), as illustrated in FIG. 18. In addition, a display device or display 600 that displays operation information of the air cleaner may be provided at an upper portion of the flow adjusting device 300. The display device 600 may be movable together with the flow adjusting device 300.

Figure 2:
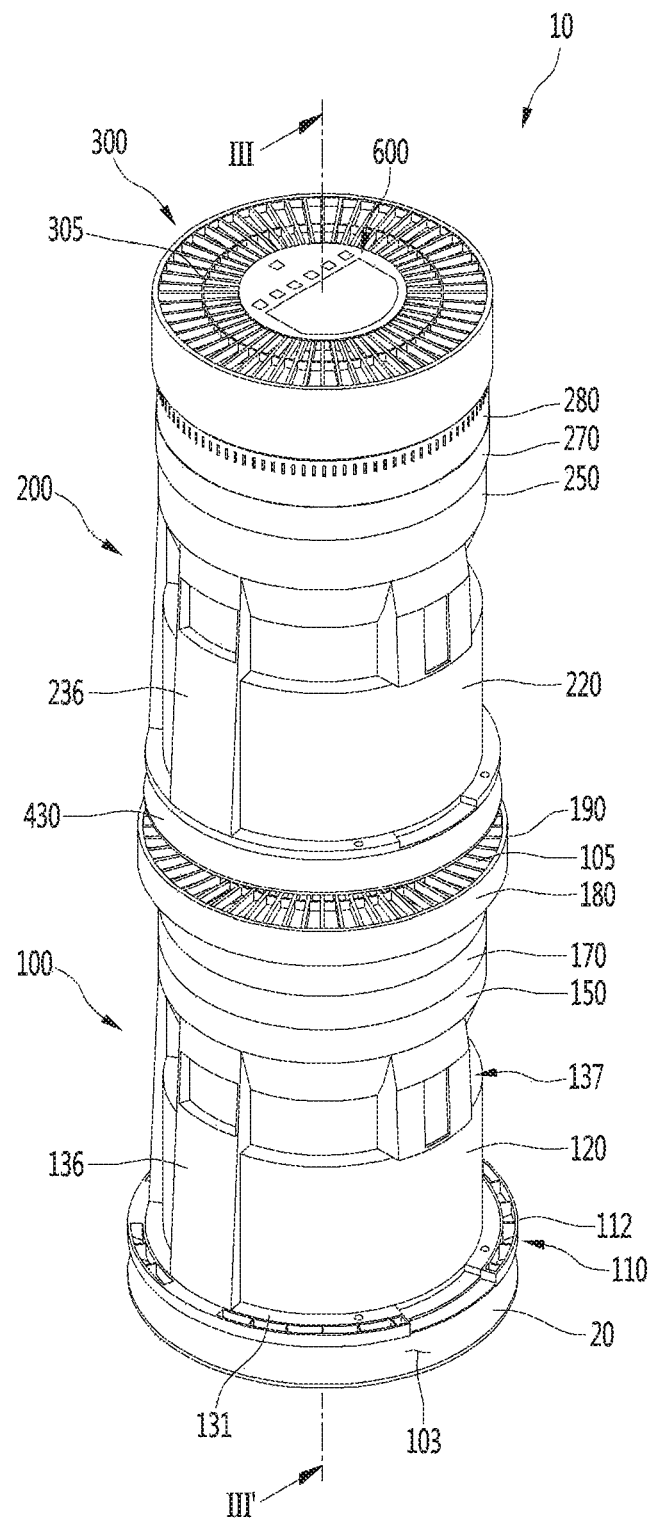
FIG. 2 is a perspective view illustrating an internal configuration of the air cleaner of FIG. 1.
Figure 3:
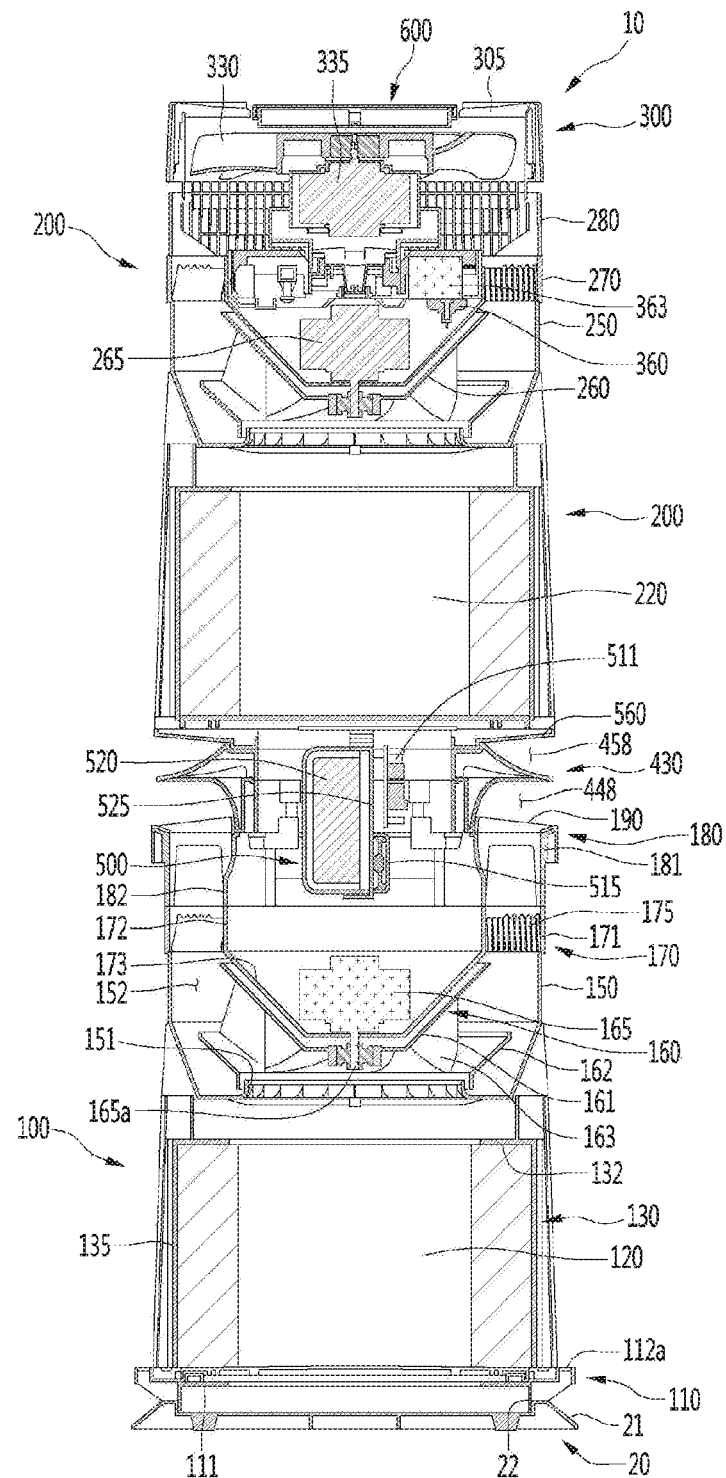
FIG. 3 is a cross-sectional view, taken along line III-III' in FIG. 2.

FIG. 2 is a perspective view of the air cleaner of FIG. 1. FIG. 3 is a cross-sectional view, taken along line III-Ill' of FIG. 2.

Referring to FIGS. 2 and 3, a base 20 and a suction grill 110, which may be disposed or provided on or at an upper side of the base 20 may be included in the first blowing device 100 according to this embodiment. The base 20 may include a base main body 21, which may be placed on the ground, and a base projecting portion or projection 22 that projects from the base main body 21 in the upward direction and on which the suction grill 110 may be placed. The base projecting portion 22 may be provided at both sides of the base 20.

The base main body 21 and the suction grill 110 may be spaced apart from each other by the base projecting portion 22. The base suction portion 103 which forms a suction space of air may be included between the base 20 and the suction grill 110.

The suction grill 110 may include a grill main body 111 having a substantially ring shape and a rim portion or rim 110 that protrudes from an outer circumferential surface of the grill main body 111 in the upward direction. By the configuration of the grill main body 111 and the rim portion 111a, the suction grill 110 may have a stepped structure.

The suction grill 110 may include a suction portion or inlet 112 formed on the rim portion 111a. The suction portion 112 may protrude along a circumference of the rim portion 111a in the upward direction and extend in a circumferential direction. In addition, a plurality of suction holes 112a may be formed in the suction portion 112. The plurality of suction holes 112a may communicate with the base suction portion 103.

Air suctioned in through the plurality of suction holes 112a and the base suction portion 103 may pass through a first filter member or filter 120. The first filter may have a cylindrical shape and a filter surface that filters air. The air passing through the plurality of suction holes 112a may be introduced to an inside portion of the first filter 120 by passing through an outer circumferential surface of the cylindrical first filter 120.

The first blowing device 100 may further include a first filter frame 130, which may form a mounting space of the first filter 120. That is, the first filter frame 130 may include a first frame 131 which forms a lower portion of the first filter frame 130 and a second frame 132 which forms an upper portion of the first filter frame 130.

The first filter frame 130 may further include a first filter supporting portion or support 135 that extends from the first frame 131 to the second frame 132 in the upward direction. The first frame 131 and the second frame 132 may be spaced apart from each other by the first filter supporting portion 135. A plurality of first filter supporting portions 135 may be provided and the plurality of the first filter supporting portions 135 may be arranged in the circumferential direction, and thus, may be connected to rim portions or rims of the first frame 131 and the second frame 132. A mounting space of the first filter 120 is defined by the plurality of first filter supporting portions 135 and the first frame 131 and the second frame 132. In addition, a first supporting portion cover 136 may be coupled to an outside of the first filter supporting portion 135.

A sensor device or sensor 137 may be installed or provided in or on the first filter frame 130. The sensor device 137 may include a dust sensor that senses an amount of dust in the air and a gas sensor that senses an amount of gas in the air. The dust sensor and the gas sensor may be disposed or provided to be supported by the second frame 132 of the first filter frame 130.

The first filter 120 may be detachably mounted in the mounting space. The first filter 120 may have a cylindrical shape and air may be introduced through the outer circumferential surface of the first filter 120. Impurities, such as fine dust in air, may be filtered in a process of passing through the first filter 120.

The air may be introduced from any direction relative to the first filter 120, by the first filter 120 having the cylindrical shape. Accordingly, a filtering area of air may be increased.

The mounting space may have a cylindrical shape corresponding to the shape of the first filter 120. The first filter 120 may be slidably introduced toward the mounting space in a mounting process. In contrast, the first filter 120 may be slidably withdrawn from the mounting space in a separating process.

The first blowing device 100 may further include a first fan housing 150, which may be installed or provided on or at an outlet side of the first filter 120. A housing space portion or space 152, in which a first fan 160 may be accommodated, may be formed in the first fan housing 150. In addition, the first fan housing 150 may be supported by the first filter frame 130.

A first fan introducing portion 151 that guides introduction of air to an inside of the first fan housing 150 may be included in a lower portion of the first fan housing 150. A grill may be provided in or on the first fan introducing portion 151 to prevent, for example, a finger of a user from being put into the inside of the first fan housing 150 when the first filter 150 is separated.

The first blowing device 100 may further include an ionizer 158 that removes or sterilizes smell particles in the air. The ionizer 158 may be coupled to the first fan housing 150 and be capable of acting on the air which flows inside of the first fan housing 150.

The sensor device 137 and the ionizer 158 may also be installed or provided in a second blowing device 200 described hereinafter. For example, the sensor device 137 and the ionizer 158 may be installed or provided in one of the first blowing device 100 or the second blowing device 200.

The first fan 160 may be located on or at an the upper side of the first fan introducing portion 151. For example, the first fan 160 may include a centrifugal fan that introduces air in the axial direction and then discharges air to the upper side in the radial direction.

The first fan 160 may include a hub 161 to which a rotational shaft 165*a* of a first fan motor 165, which may be a centrifugal fan motor, may be coupled, a shroud 162 which may be disposed or provided in a state of being spaced apart from the hub 161, and a plurality of blades 163, which may be disposed or provided between the hub 161 and the shroud 162. The first fan motor 165 may be coupled to the upper side of the first fan 160.

The hub 161 may have a bowl shape, a diameter of which may be gradually reduced in the downward direction. The hub 161 may include a shaft coupling portion to which the rotational shaft 165*a* may be coupled and a first blade coupling portion that extends at an incline from the shaft coupling portion in the upward direction.

The shroud 162 may include a lower end portion or end, on or at which a shroud suction port, into which air having passed through the first fan introducing portion 151 may be suctioned, may be formed and a second blade coupling portion that extends from the lower end portion in the upward direction.

A first surface of each blade 163 may be coupled to the first blade coupling portion of the hub 161 and a second surface thereof may be coupled to the second blade coupling portion of the shroud 162. The plurality of blades 163 may be disposed or provided spaced apart in a circumferential direction of the hub 161.

The first blowing device 100 may further include a first air guide device or guide 170 that guides a flow of air being passed through the first fan 160 by being coupled to an upper side of the first fan 160.

The first air guide 170 may include an outer wall 171 having a cylindrical shape and an inner wall 172 positioned on or at an inside of the outer wall 171 and having a cylindrical shape. The outer wall 171 may be disposed or provided to surround the inner wall 172. A first air flow path 172*a*, through which air may flow may include circumferential surface of the outer wall 171 and an outer circumferential surface of the inner wall 172.

The first air guide 170 may include a guide rib 175 which may be disposed or provided on or in the first air flow path 172*a*. The guide rib 175 may extend from the outer circumferential surface of the inner wall 172 to the inner circumferential surface of the outer wall 171. A plurality of guide ribs 175 may be disposed or provided spaced apart from each other. The plurality of guide ribs 175 may guide the air introduced to the first air flow path 172*a* of the first air guide 170 via the first fan 160 in the upward direction.

The guide rib 175 may extend at an incline from a lower portion of the outer wall 171 and the inner wall 172 in the upward direction. For example, the guide rib 175 may be rounded, and thus, guide air so that it flows at an incline in the upward direction.

The first air guide 170 may further include a motor accommodating portion 173 that extends from the inner wall 172 to the lower side, and thus, accommodates the first fan motor 165. The motor accommodating portion 173 may have a bowl shape, a diameter of which may be gradually reduced in the downward direction. A motor coupling portion 166 may be provided on or at one side of the first fan motor 165 to fix the first fan motor 165 to the first air guide 170. A shape of the motor accommodating portion 173 may correspond to the shape of the hub 161. The motor accommodating portion 173 may be inserted into the hub 161.

The first fan motor 165 may be supported to or at an upper side of the motor accommodating portion 173. The rotational shaft 165*a* of the first fan motor 165 may extend from the first fan motor 165 in the downward direction and be coupled to the shaft coupling portion 161a of the hub 161 through the lower surface portion of the motor accommodating portion 173.

The first blowing device 100 according to this embodiment may further include a second air guide device or guide 180 which may be coupled to an upper side of the air guide 170 and guide air having passed through the first air guide 170 to the discharge guide 190.

The second air guide 180 may include a first guide wall 181, which may have a substantially cylindrical shape, and a second guide wall 182, which may be positioned at an inside of the first guide wall 181 and have a substantially cylindrical shape. The first guide wall 181 may be disposed or provided to surround the second guide wall 182.

A second air flow path 185, through which air may flow, may be formed between an inner circumferential surface of the first guide wall 181 and an outer circumferential surface of the second guide wall 182. Air which flows along the first air flow path 172a of the first air guide 170 may flow in the upward direction through the second air flow path 185. The second air flow path 185 may be referred to as a "discharge flow path." In addition, the first discharge portion 105 may be provided on or at an upper side of the second air flow path 185.

A space portion or space, in which at least a portion of a printed circuit board (PCB) device 500 may be accommodated by passing therethrough in the vertical direction may be formed inside of the second guide wall 182 having a cylindrical shape. The PCB device 500 may include a power supply portion or power supply 520 and a main PCB 511.

The power supply portion 520 may refer to a device that receives commercial power supplied from a power line connected to the air cleaner 10 to supply power to the main PCB 511 and a plurality of components in the air cleaner 10. The power supply 520 may include a PCB (power PCB) for AC power. The main PCB 511 may include a PCB for DC power, which may be driven by a DC voltage converted in the PCB for AC power.

The PCB device 500 may further include a PCB supporting plate 525 that supports the power supply portion 520 and the main PCB 511. The main PCB 511 may be supported on one or a first surface of the PCB supporting plate 525, and the power supply portion 520 may be supported on the other or a second surface of the PCB supporting plate 525.

The PCB device 500 may include a communication module 515 through which the air cleaner 10 is capable of communicating with an external device. For example, the communication module 515 may include a Wi-Fi module. The communication module 515 may be supported on the PCB supporting plate 525, and may be disposed or provided at a lower side of the main PCB 511.

The first blowing device 100 may further include a first discharge guide device or guide 190, which may be disposed or provided on or at an upper side of the second air guide 180, that is, an outlet side of air flow passing through the second air guide 180 relative to the air flow and guide the air discharge to outside of the air cleaner 10. A first discharge portion 105, through which air may be discharged, may be formed in the first discharge guide 190.

Figure 4:
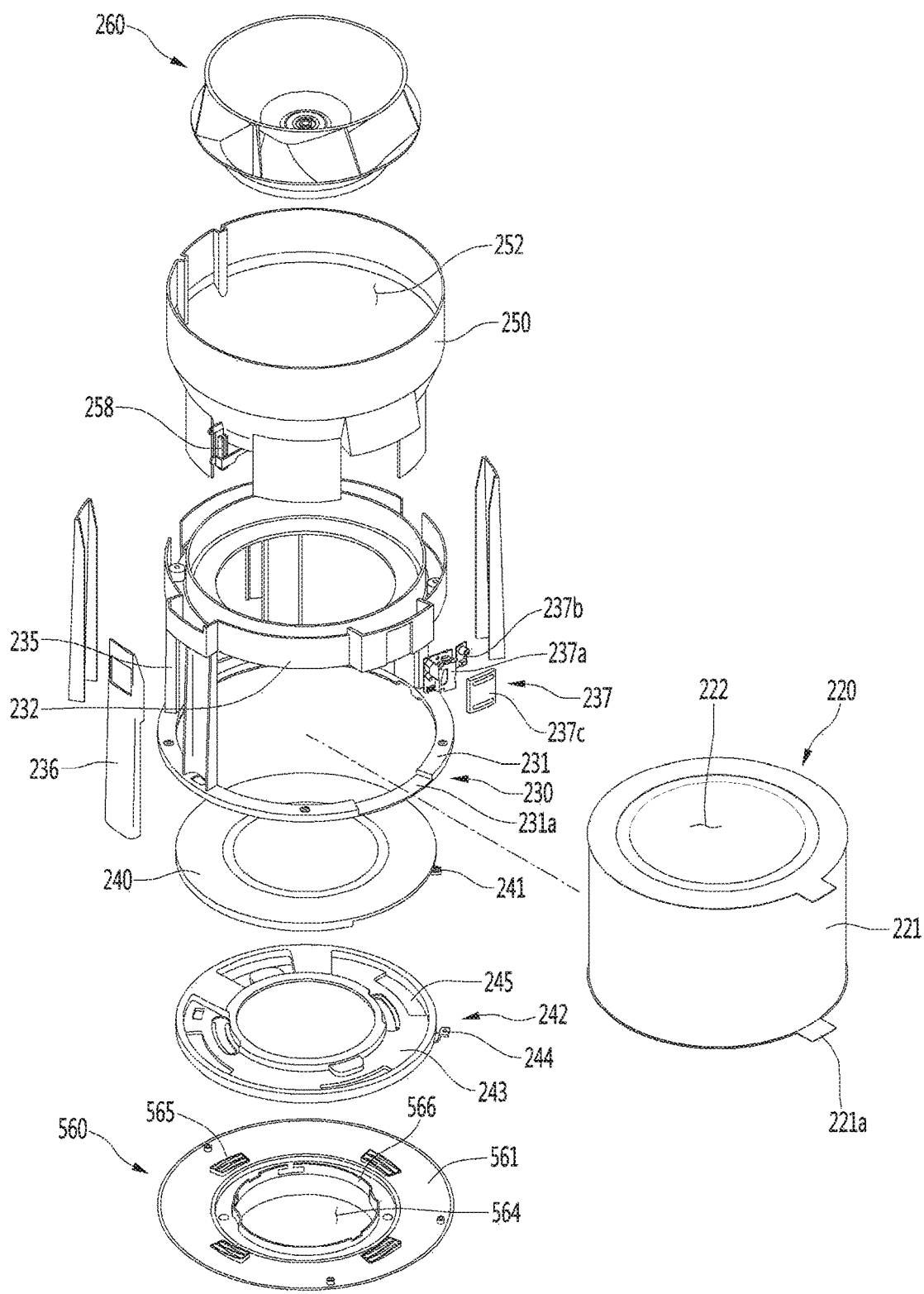
FIG. 4 is an exploded perspective view of a second blowing device of the air cleaner of FIG. 1.

The second blowing device 200 may include a second filter member or filter 220, a supporting device or support 240 that supports a lower portion of the second filter 220, and a lever device or lever 242 provided on or at a lower side of the supporting device 240 to support the second filter 220 and the supporting device 240 (see FIG. 4).

The second blowing device 200 may further include a lever supporting device or support 210 that supports the second filter 220 or the lever device of the second blowing device 200. The lever supporting device 560 may have a substantially annular shape. The lever supporting device 560 may include a space portion or space which defines an installation space portion or space, in which the PCB device 500 may be located. The space portion may be formed at a substantially center portion of the lever supporting device 560 by passing through the lever supporting device 560 in the vertical direction.

A dividing device 400 may be provided between the first blowing device 100 and the second blowing device 200. The dividing device 400 may include a dividing plate 430 that separates or blocks air flow generated in the first blowing device 100 and air flow generated in the second blowing device 200. By the dividing plate 430, the first and second blowing devices 100 and 200 may be spaced apart from each other in the vertical direction.

That is, a separation space in which the dividing plate 430 may be located or provided may be formed between the first and second blowing devices 100 and 200. The first discharge guide 190 of the first blowing device 100 may be located at a lower end portion or end of the separation space, and the lever supporting device 510 of the second blowing device 200 may be located at an upper end portion or end of the separation space.

The separation space may be divided into an upper space and a lower space by the dividing plate 430. The lower space may be a first space portion or space through which air discharged from the first discharge portion 105 of the first discharge guide 190 may pass in a process in which the air flows to the outside of the air cleaner 10. The upper space may be a second space portion or space that functions as a grasping space into which a user may put his or her hand when moving the air cleaner 10.

Air discharged from the first discharge portion 105 may be guided by the dividing plate 430 to flow to the outside of the air cleaner 10. Accordingly, it is possible to prevent the air from being introduced into the second blowing device 200.

FIG. 4 is an exploded perspective view of the second blowing device of the air conditioner of FIG. 1. Referring to FIG. 4, the second blowing device 200 according to this embodiment may include the lever supporting device 560, a lever device 242, the supporting device or support 240, the second filter 220, the second filter frame 230, a second fan housing 250, and a second fan 260.

The second filter 220 may have a cylindrical shape having an open upper portion. The second filter 220 may include a filter main body 221, which may have a cylindrical filter portion an inside of which is empty, and a filter hole 222, which may be opened at an upper end portion or end of the filter main body 221. A filter grasping portion or grasp 221a may be provided at an upper or lower portion of the filter main body 221. Air may be introduced to the inside of the filter main body 221 through an outer circumferential surface of the filter main body 221, and may be discharged from the second filter 220 through the filter hole 222. The second filter 220 may be the same as or similar to the first filter 120, and thus, repetitive disclosure has been omitted.

The lever supporting device 560 may include a lever supporting main body 561 having an annular shape. The lever supporting main body 561 may extend at a slight incline in the upward direction with respect to the axial direction toward an outer circumferential surface from an inner circumferential surface thereof. That is, a surface which forms the lever supporting main body 561 may be an inclined surface. A space between the inclined surface and an upper surface of the dividing plate 430 may provide a space portion or space 458 in which a user's hand may be located. The lever supporting main body 561 may be referred to as a "blocking portion" in that air discharged through the first discharge portion 105 of the first blowing device 100 may be blocked from being introduced to the second blowing device 200.

The lever supporting device 560 may further include a movement guide portion or guide 565, which may protrude from the lever supporting main body 561 in the upward direction. A plurality of movement guides 565 may be spaced apart from one another in a circumferential direction of the lever supporting main body 561. In addition, the lever supporting device 560 may further include a supporting projection 566 that protrudes in the upward direction from an inner circumferential surface of the lever supporting main body 561. The supporting projection 566 may support the lever device 242 of the second blowing device 200.

The lever device 242 may be operable by a user. For example, the lever device 242 may be rotatable in the circumferential direction. The lever device 242 may include a lever main body 243, which may have a substantially ring shape and be rotatable. In addition, a plurality of cut-out portions or cut-outs 245, which may be disposed or provided at positions corresponding to the plurality of movement guides 565, may be formed in the lever main body 243.

The plurality of cut-out portions 245 may be spaced apart from one another, and arranged in the circumferential direction of the lever main body 243. In addition, each of the plurality of cut-out portions 245 may be rounded with a predetermined curvature in the circumferential direction, corresponding to a curvature of the outer circumferential surface of the lever main body 243.

The lever device 142 may be supported on an upper surface of the lever supporting main body 561. If the lever device 242 is supported by the lever supporting main body 561, the plurality of movement guides 565 may be inserted into the plurality of cut-out portions 245. That is, the plurality of movement guides 565 may protrude to the upper side of the plurality of cut-out portions 245 by passing through the plurality of cut-out portions 245.

A length of each of the plurality of cut-out portions 245 may be longer than a length of the movement guide 565. Thus, the lever device 242 may rotate in a state in which the movement guide 565 is inserted into the cut-out portion 245. In addition, one end portion or end of the movement guide 565 may interfere with one end portion or end of the cut-out portion 245 in a process in which the lever device 242 rotates in one or a first direction, and the other end portion or end of the movement guide 565 may be interfere with the other end portion or end of the cut-out portion 245. A second handle 244 may be provided on an outer circumferential surface of the lever main body 243.

The supporting device 240, which supports the second filter 220, may be provided on or at an upper side of the lever device 242. The supporting device 240 may include a first handle 241 which may be coupled to the second handle 244. A user may rotate the lever main body 143 and the supporting device 140 in a clockwise direction or in a counterclockwise direction by grasping the first and second handles 241 and 244. The lever device 242 may support a lower surface of the supporting device 240. The supporting device 240 may include a support projecting portion or projection (not shown), which may be in contact with the movement guide 565. The support projecting portion may protrude in the downward direction from a lower surface of the supporting device 240, and may be provided at a position corresponding to the movement guide 565. In addition, a shape of the support projecting portion may correspond to a shape of the movement guide 565, and include an inclined surface that gradually protrudes in the circumferential direction. In addition, a direction in which the movement guide 565 gradually protrudes and a direction in which the support projecting portion gradually protrudes may be opposite to each other.

For example, if the direction in which the movement guide 565 protrudes is the counterclockwise direction, the direction in which the support projecting portion protrudes may be the clockwise direction. The support projecting portion may be disposed or provided at a position corresponding to the cut-out portion 245. That is, the movement guide 565 and the support projecting portion may be disposed or provided at a position at which they are inserted into the cut-out portion 245.

The lever device 242 and the supporting device 240 may rotate together. In the rotation process, the movement guide 565 and the support projecting portion may interfere with each other. That is, if a lower portion of the support projecting portion and an upper portion of the movement guide 565 are in contact with each other, the lever device 242 and the supporting device 240 may be lifted in the upward direction. In addition, the second filter 220 supported by the supporting device 240 may be in a state in which the second filter 220 is coupled to the second blowing device 200 while moving in the upward direction.

On the other hand, if the lower portion of the support projecting portion and the upper portion of the movement guide 565 are in contact with each other or if the inference between the support projecting portion and the movement guide 565 is released, the lever device 242 and the supporting device 240 may move downward. In addition, the second filter 220 supported by the supporting device 240 may be in a state (released state) in which the second filter 220 is separable from the second blowing device 200.

The second blowing device 200 may include a second filter frame 230, which may form a mounting space for the second filter 220. That is, the second filter frame 230 may include a first frame 231, which may form a lower portion of the second filter frame 230, and a second frame 232, which may form an upper portion of the second filter frame 230.

The first frame 231 may include a frame depression portion or depression 231*a* having a downwardly depressed shape. The frame depression portion 231*a* may be configured such that at least a portion of the first frame 231 is depressed. The frame depression portion 231*a* may provide a space portion or space, in which the first and second handles 241 and 244 may be movable. The first and second handles 241 and 244 may be located in the space portion, to rotate in the clockwise direction or in the counterclockwise direction.

The second frame 232 may be spaced apart from the first frame 231 in the upward direction. The second frame 232 may have a substantially ring shape. The ring-shaped inside portion space of the second frame 232 may form at least a portion of an air flow path passing through the second filter frame 230. In addition, an upper portion of the second frame 232 may support the second fan housing 250.

The second filter frame 230 may further include a second filter supporting portion or support 235 that extends from the first frame 231 to the second frame 232 in the upward direction. The first frame 231 and the second frame 232 may be spaced apart from each other by the second filter supporting portion 235. A plurality of second filter supporting portions 235 may be provided, and the plurality of the first second supporting portions 235 may be arranged in the circumferential direction, and thus, may be connected to rim portions or rims of the first frame 231 and the second frame 232.

A mounting space for the second filter 220 may be defined by the first and second frames 231 and 232 and the plurality of second filter supporting portions 235. In addition, a first supporting portion cover 236 may be coupled to an outside of the second filter supporting portion 235.

A sensor device 237 may be installed or provided in or on the second filter frame 230. The sensor device 237 may include a dust sensor 237a that senses an amount of dust in the air and a gas sensor 237b that senses an amount of gas in the air. The dust sensor 237a and the gas sensor 237b may be supported by the second frame 232 of the second filter frame 230. The sensor device 237 may include a sensor cover 237c that covers the dust sensor 237a and the gas sensor 237b.

The second filter 220 may be detachably mounted on or in the mounting space. The second filter 220 may have a cylindrical shape and air may be introduced through an outer circumferential surface of the second filter 220. Impurities, such as fine dust in air, may be filtered in a process of passing through the second filter 220.

The air may be introduced from any direction relative to the second filter 220, by the second filter 220 having the cylindrical shape. Accordingly, a filtering area of air may be increased. The mounting space may have a cylindrical shape corresponding to the shape of the second filter 220. The second filter 220 may be slidably introduced toward the mounting space in a mounting process. In contrast, the second filter 220 may be slidably withdrawn from the mounting space in a separating process.

On the other hand, the second filter 220 may be slid toward the mounting space to the inside in the radial direction in a state of being separated from the mounting space, supported on the upper surface of the supporting device 240, and thus, may be moved into close contact upwardly by an operation of the first and second handles 241 and 244. At this time, the second filter 220 may be in a coupling position.

The second blowing device 200 may include a second fan housing 250, which may be installed or provided on or at an outlet side of the second filter 220. A housing space portion or space 252, in which the second fan 260 may be accommodated, may be formed in the second fan housing 250. The second fan housing 250 and the second fan 260 may be the same or similar to the first fan housing 150 and the first fan 160, and therefore, repetitive disclosure has been omitted.

The second blowing device 200 may include an ionizer 258 that removes or sterilizes smell particles in the air. The ionizer 258 may be coupled to the second fan housing 250 and may act on the air which flows inside of the second fan housing 250. The ionizer 258 may be the same as or similar to the ionizer of the first blowing device 100, and therefore, repetitive disclosure has been omitted.

Figure 5:
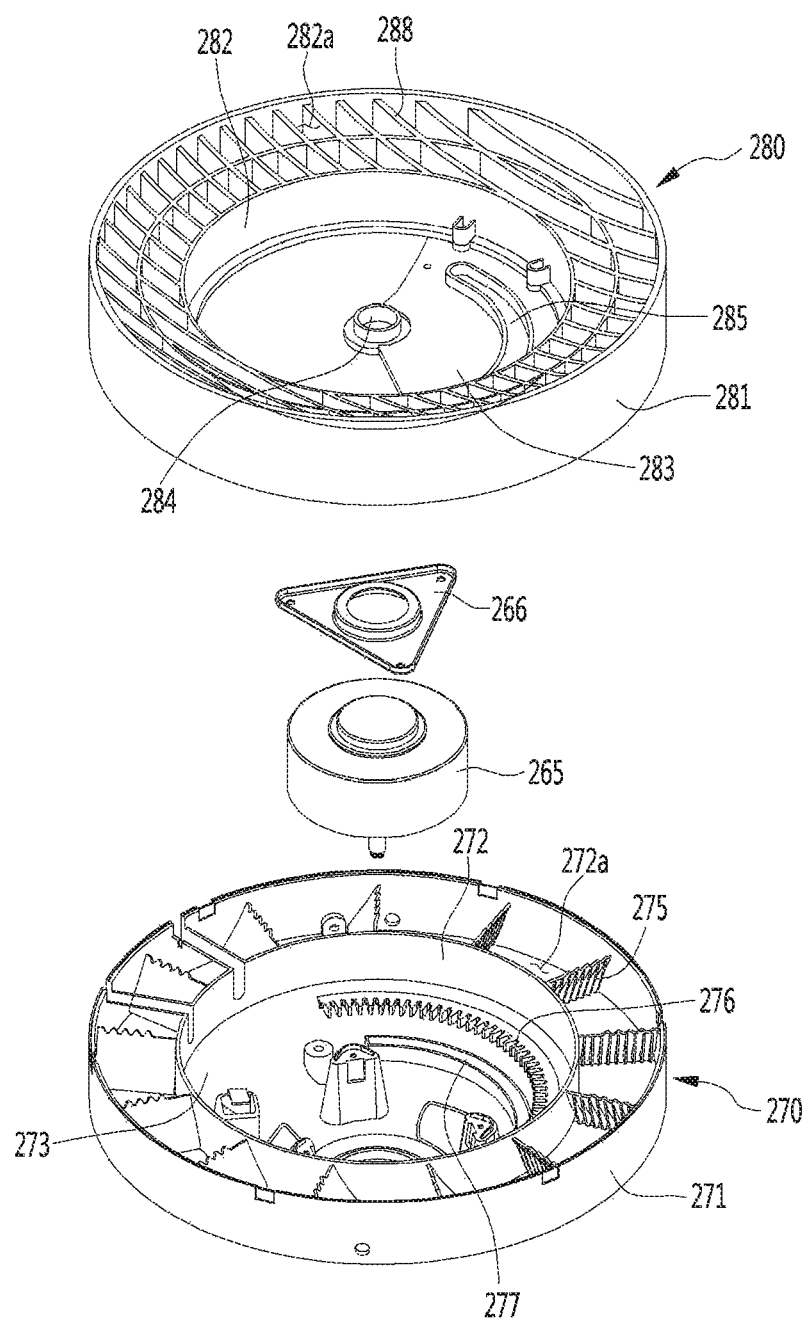
FIG. 5 is an exploded perspective view illustrating a third air guide and a second discharge guide of the air cleaner of FIG. 1.
Figure 6:
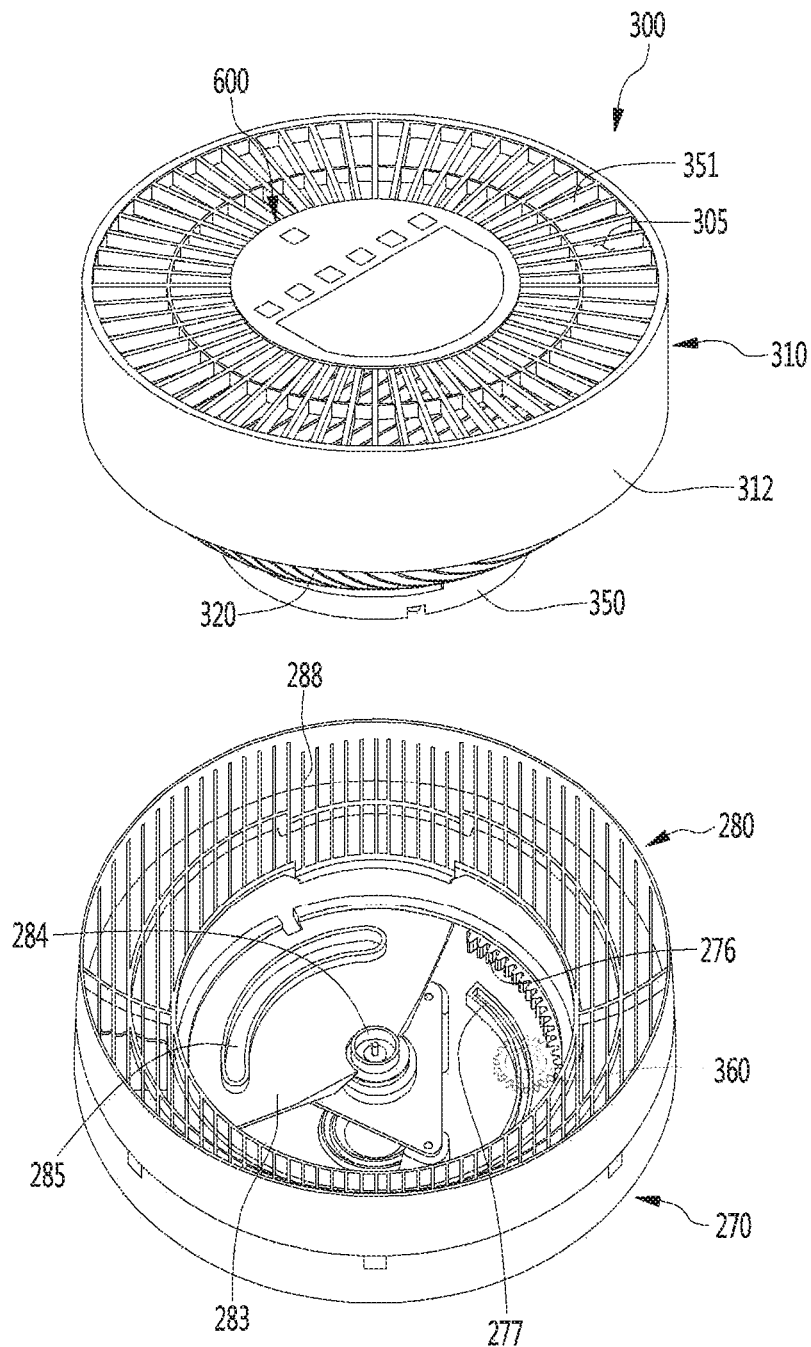
FIG. 6 is an exploded perspective view of an air flow control device and a component to which the air flow control device is coupled of the air cleaner of FIG. 1.
Figure 7:
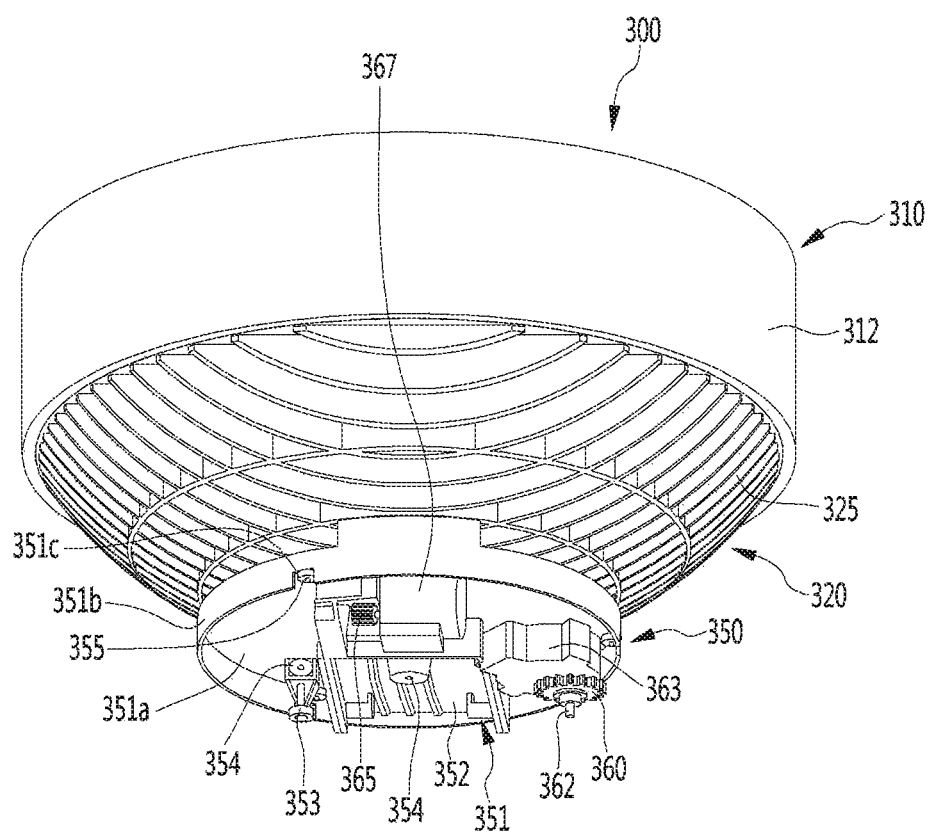
FIG. 7 is a perspective view of the air flow control device of FIG. 6.
Figure 8:
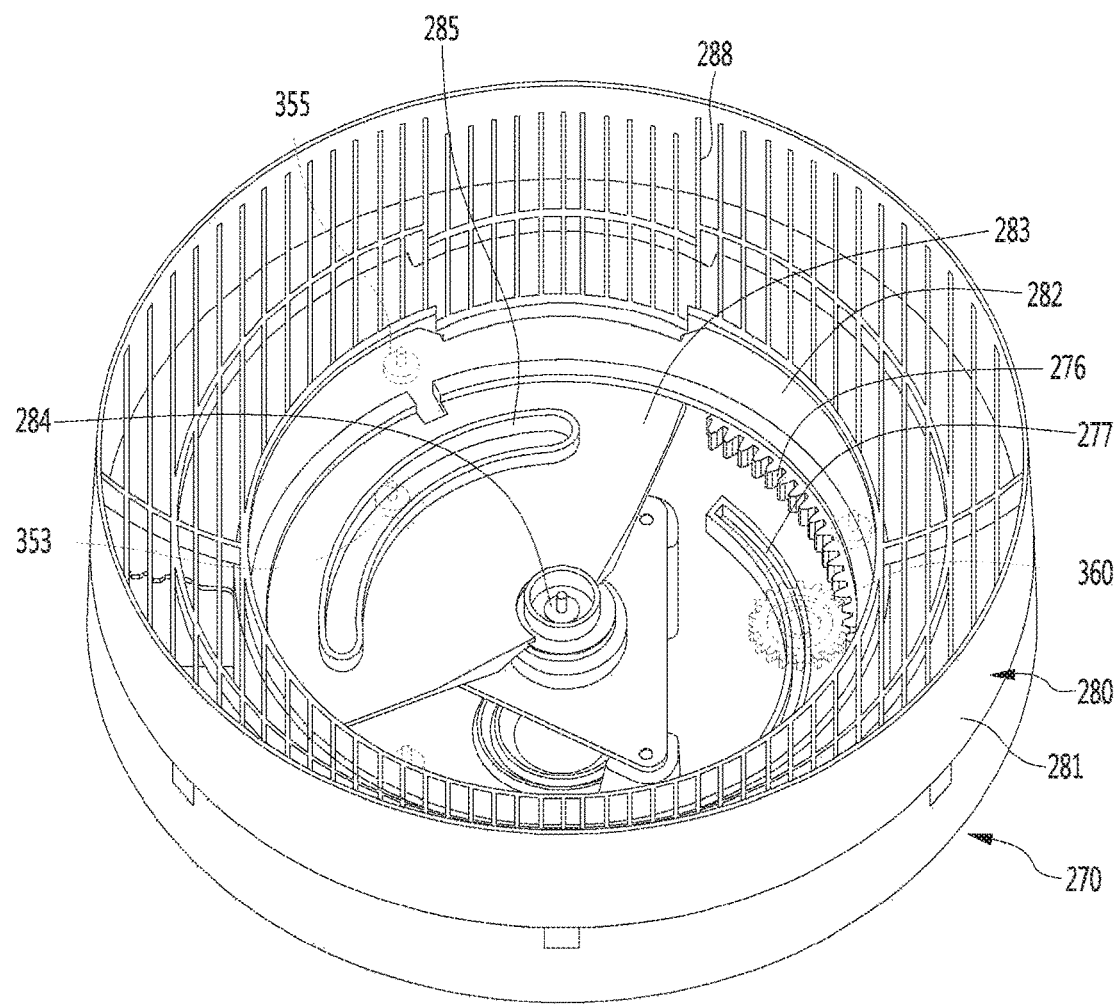
FIG. 8 is a view illustrating a state in which the third air guide and the second discharge guide of FIG. 5 are coupled to each other.
Figure 9:
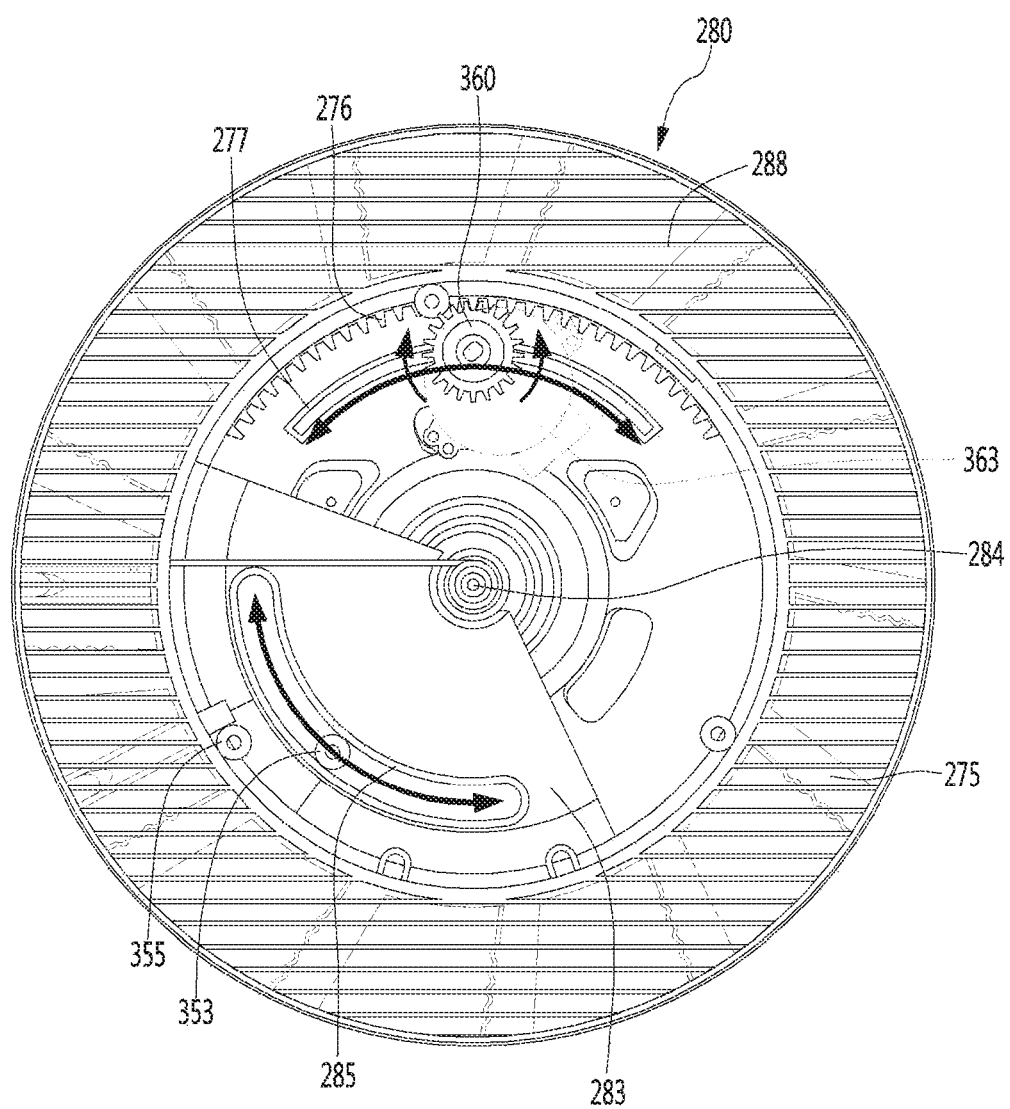
FIG. 9 is a view illustrating a state in which a first guide acts to perform rotation in a lateral direction of the air flow control device according to an embodiment.
Figure 10:
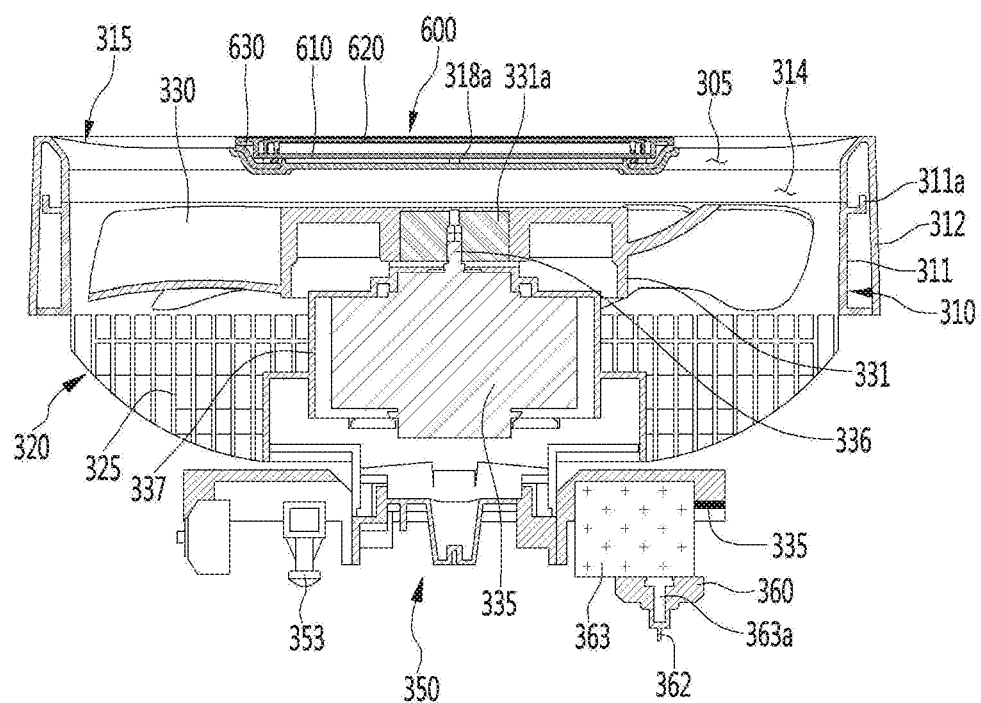
FIG. 10 is a sectional view of the air flow control device according to an embodiment.

FIG. 5 is an exploded perspective view illustrating a third air guide and a second discharge guide of the air cleaner of FIG. 1. FIG. 6 is an exploded perspective view of an air flow control device and a component to which the air flow control device is coupled of the air cleaner of FIG. 1. FIG. 7 is a perspective view of the air flow control device of FIG. 6. FIG. 8 is a view illustrating a state in which the third air guide and the second discharge guide of FIG. 5 are coupled to each other. FIG. 9 is a view illustrating a state in which a first guide acts to perform rotation in a lateral direction of the air flow control device according to an embodiment. FIG. 10 is a sectional view of the air flow control device according to an embodiment.

Referring to FIGS. 5 to 10, the second blowing device 200 may include a third air guide device or guide 270 that guides a flow of air having passed through the second fan 260 by being coupled to an upper side of the second fan 260. The third air guide 270 may include an outer wall 271 that forms an outer circumferential surface of the third air guide 270 and an inner wall 272 positioned inside of the outer wall 271 and having a cylindrical shape. A first air flow path 272a, through which air may flow, may be formed between an inner circumferential surface of the outer wall 271 and an outer circumferential surface of the inner wall 272.

The third air guide 270 may include a guide rib 275 which may be disposed or provided on or in the first air flow path 272a. The guide rib 275 may extend from the outer circumferential surface of the inner wall 272 to the inner circumferential surface of the outer wall 271.

The third air guide 270 may include a motor accommodating portion 273 that extends from the inner wall 272 in the downward direction, and thus, accommodates the second fan motor 265. The motor accommodating portion 273 may have a bowl shape a diameter of which may be gradually reduced toward a lower side thereof.

The second fan motor 265 may be coupled to the upper side of the second fan 260, and thus, provide a drive force to the second fan 260. A motor coupling portion 266 may be provided on or at one side of the second fan motor 265, and the motor coupling portion 266 may fix the second fan motor 265 to the third air guide 270.

The third air guide 270 may include guide devices or guides 276 and 277 that guide a movement of the flow adjusting device 300. The guides 276 and 277 may include a first rack 276 and a shaft guide groove 277, which may be included in the motor accommodating portion 273.

The first rack 276 may be linked to the first gear 360 of the flow adjusting device 300. The first rack 276 may be provided on or at an inner circumferential surface of the motor accommodating portion 273 and may be provided along a set predetermined curvature in the circumferential direction. A length of the first rack 276 may be a length which is set based on a distance linked to the first gear 360.

The flow adjusting device 300 may be rotated in the lateral direction, that is, in the clockwise direction or in the counterclockwise direction. In this process, the first gear 360 may be rotated along a predetermined rotating radius about a rotational shaft 354 of the flow adjusting device 300.

The shaft guide groove 277 may be a groove that guides rotation of the first gear 260 and may extend rounded with a predetermined curvature. For example, the shaft guide groove 277 may be rounded in the circumferential direction. That is, the shaft guide groove 277 may have an arc shape.

The first gear shaft 362 of the first gear 360 may be inserted into the shaft guide groove 277. In a process of rotation of the first gear 360, the first gear shaft 360 may be moved along the shaft guide groove 277.

The second blowing device 200 may include a second discharge guide 280, which may be installed on or at an upper side of the third air guide 270 and guide a flow of air which passed through the third air guide 270. The second discharge guide 280 may have a substantially annular shape an inside portion of which may be empty. That is, the second discharge guide 280 may include a discharge outer wall 281, which may form an outer circumferential surface of the second discharge guide 280 and have a cylindrical shape, and a discharge inner wall 282 which may form an inner circumferential surface of the second discharge guide 280 and have a cylindrical shape.

The discharge outer wall 281 may surround the discharge inner wall 282. A second air flow path 282a, that is, a discharge flow path along which air passing through the third air guide 270 may flow, may be formed between an inner circumferential surface of the discharge outer wall 281 and an outer circumferential surface of the discharge inner wall 282. The discharge flow path may be positioned on or at an upper side of the first air flow path 272a, in which the guide rib 275 may be provided.

The second discharge guide 280 may include a second discharge grill 288, which may be disposed or provided on or in the discharge flow path 282a. The second discharge grill 288 may extend from the outer circumferential surface of the discharge inner wall 282 to the inner circumferential surface of the discharge outer wall 281.

The second discharge guide 280 may further include a rotation guide plate 283, which may be coupled to the discharge inner wall 282. The rotation guide plate 283 may extend from the inner circumferential surface of the discharge inner wall 282 toward an inside center of the second discharge guide 280.

The rotation guide plate 283 may include a shaft inserting portion 284, which may provide a rotational center in the lateral direction of the flow adjusting device 300. The rotational shaft 354 may be inserted into the shaft inserting portion 284. The shaft inserting portion 284 may be positioned in the inside central portion of the second discharge guide 280. The rotation guide plate 283 may be a supporting plate that supports the shaft inserting portion 284.

A bearing groove 285 may be further included in the rotation guide plate 283. A first bearing 353, which may be provided on the flow adjusting device 300, may be inserted into the bearing groove 285. The bearing groove 285 may guide movement of the first bearing 353 and extend to be rounded with a predetermined curvature. For example, the bearing groove 285 may be rounded in the circumferential direction. That is, the bearing groove 285 may have an arc shape. In a process of rotation of the flow adjusting device 300 in the lateral direction, the first bearing 353 may be moved by inserted into the bearing groove 285, and thus, allows a friction force which is generated in the process of rotation of the flow adjusting device 300 to be reduced.

The flow adjusting device 300 may include a third fan housing 310, in which a third fan 330 may be accommodated. The third fan housing 310 may have a substantially annular shape. For convenience of description, the first fan 160 and the second fan 260 may be referred to as a "blowing fan," and the third fan 330 may be referred to as a "circulation fan." That is, the first fan 160 and the second fan 260 may be referred to as a "main fan," and the third fan 330 may be referred to as a "sub-fan."

The third fan housing 310 may include a housing cover 312, which may form an outer appearance thereof. A housing main body 311, which may have an annular shape, may be provided inside of the housing cover 312. That is, the housing cover 312 may be coupled to an outer circumferential surface of the housing main body 311, and may be supported by the housing main body 311.

The housing main body 311 may include a cover supporting portion or support 311a, which may protrude from an outer circumferential surface of the housing main body 311 to support an inside of the housing cover 312. The cover supporting portion 311a may have a bent shape, and an outer surface of the cover supporting portion 311a may be coupled to an inner surface of the housing cover 312.

The housing cover 312 may surround the housing main body 311, and the housing main body 311 and the housing cover 312 may be rotated or moved together. The third fan 330 may be accommodated inside of the housing main body 311. In addition, a housing flow path 314, through which air may flow as the third fan 330 is driven, may be formed inside of the housing main body 311. A blade 333 of the third fan 330 may be located in the housing flow path 314. By rotation of the blade 333, air may flow in the upward direction via the housing flow path 314. The housing flow path 314 may extend from a space in which the blade 333 is located to an upper space of the blade 333.

A discharge grill 315, which may form the second discharge portion 305 through which air passing through the third fan 330 may be discharged, may be provided on or at an upper side of the third fan housing 310. That is, referring to FIG. 17, the discharge grill 315 may include a grill outer wall 316, a grill inner wall 317 provided at an inside of the grill outer wall 316, and a plurality of grill portions 315a, which may extend from the grill outer wall 316 to the grill inner wall 317. Spaces between the plurality of grill portions 315a may form the second discharge portion 305.

As the second discharge portion 305 along with the first discharge portion 105 of the first blowing device 100 is provided in the air cleaner 10, a discharge amount of air may be improved, and air may be discharged in various directions.

Each of the grill outer wall 316 and the grill inner wall 317 may have a cylindrical shape, and the grill outer wall 316 may surround the grill inner wall 317. In addition, the second discharge portion 305 may be formed on or at an upper side of the housing flow path 314. Thus, air having passed through the housing flow path 314 may be discharged outside of the air cleaner 10 via the second discharge portion 305 of the discharge grill 315.

The discharge grill 315 may further include a depression portion or depression 318 which may have a shape depressed at a substantially center portion of the discharge grill 315 and support the display device 600. The depression portion 318 may be provided in or at a lower end portion or end of the grill inner wall 317.

A supporting rib 318a that supports a display PCB 610 of the display device 600 may be provided in the depression portion 318. The supporting rib 318a may protrude in the upward direction from an upper surface of the depression portion 318. The grill inner wall 317 may support a lower side of the display PCB 610.

The display device 600 may include a PCB assembly 601. The PCB assembly 601 may include the display PCB 610, on which an illumination source may be provided, a reflector 620, which may be coupled to an upper side of the display PCB 610 and concentrate light irradiated from the illumination source in the upward direction such that displayed information may be displayed as various characters, numbers, or symbols, and a diffusing plate 630, which may be supported on the discharge grill 315 and guide light irradiated from the illumination source to be refracted and then face an upper surface of the display device 600, that is, a rim portion or rim 650 of a display screen 602.

An axial flow fan may be included in the third fan 330. That is, the third fan 330 may be operated in order to axially discharge air which is axially introduced. That is, the air which flows toward the third fan 330 in the upward direction via the second fan 260, the first air flow path 272a of the third air guide 270, and the discharge flow path 282a of the second discharge guide 280 may be discharged from the third fan 330, and thus, may be discharged to the outside through the second discharge portion 305, which may be positioned on the upper side of the third fan 330.

The third fan 330 may include a hub 331 having a shaft coupling portion to which a rotational shaft 336 of the third fan motor 335, which may be an axial flow motor, may be coupled, and a plurality of blades 333, which may be coupled to the hub 331 in the circumferential direction. The third fan motor 335 may be coupled to a lower side of the third fan 330 and may be disposed or provided inside of the third motor housing 337.

The first fan motor 165 and the second fan motor 265 may be disposed or provided in series relative to a longitudinal direction of the air cleaner 10. The second fan motor 265 and the third fan motor 335 may be disposed or provided in series relative to a longitudinal direction of the air cleaner 10. In summary, rotational shafts of the first fan motor 165, the second fan motor 265, and the third fan motor 335, or the first fan 160, the second fan 260, and the third fan 330 may be positioned on a same axis in the longitudinal direction.

The flow adjusting device 300 may include a flow guide portion or guide 320, which may be coupled to a lower side of the third fan housing 310, and thus, guide the air passing by the second discharge guide 280 to the third fan housing 310. The flow guide 320 may include an introduction grill 325 that guides the air introduction to the third fan housing 310. The introduction grill 325 may have a concave shape in the downward direction.

A shape of the second discharge grill 288 of the second discharge guide 280 may be formed in a concave shape in the downward direction corresponding to a shape of the introduction grill 325. The introduction grill 325 may be seated on an upper side of the second discharge grill 288. By this configuration, the introduction grill 325 may be stably supported by the second discharge grill 288.

The flow adjusting device 300 may further include a rotation guide device or guide 350, which may be installed or provided on or at a lower side of the flow guide 320, and thus, may guide rotation in the lateral direction and rotation in the vertical direction of the flow adjusting device 300. The rotation in the lateral direction may be referred to as a "first direction rotation" and the rotation in the vertical direction may be referred to as a "second direction rotation."

The rotation guide 350 may include a guide main body 351, which may be coupled to the movement guide 320. The guide main body 351 may include a lower surface portion 351a, at which the first and second guides may be installed or provided, and a rim portion or rim 351b, which may be provided on or at a rim of the lower surface portion 351a and protrude in the downward direction.

The rotation guide 350 may include a first guide mechanism or guide that guides the first direction rotation of the flow adjusting device 300, and a second guide mechanism or guide that guides the second direction rotation of the flow adjusting device 300. The first guide mechanism may include a first gear motor 363 that generates a drive force, and a first gear 360 rotatably coupled to the first gear motor 363. For example, the first gear motor 363 may include a step motor, a rotational angle of which may be easily controlled.

The first gear 360 may be coupled to a motor shaft 363a of the first gear motor 363. The first guide may further include a first gear shaft 362 that extends in the downward direction, that is, toward the third air guide 270 or the second discharge guide 280 from the first gear 360. The first gear 360 may be geared to the first rack 276 of the third air guide 270. A plurality of gear teeth may be formed in the first gear 360 and the first rack 276. When the first gear motor 363 is driven, the first gear 360 may rotate, and thus, link to the first rack 276. The third air guide device 270 may be fixed, and thus, the first gear 360 may be movable.

The shaft guide groove 277 of the third air guide 270 may guide movement of the first gear 360. That is, the first gear shaft 362 may be inserted into the shaft guide groove 277. The first gear shaft 362 may be moved in the circumferential direction along the shaft guide groove 277 in a rotation process of the first gear 360.

The first guide may include the rotational shaft 354, which may form a rotational center of the flow adjusting device 300. The first gear 360 and the first gear shaft 362 may be rotated along a rotating radius, which may be set about the rotational shaft 354. The set rotating radius may be referred to as a "first rotating radius."

The first rack 276 and the shaft guide groove 277 may have a length corresponding to a rotational amount or rotational angle of the flow adjusting device 300. A length in the circumferential direction of the first rack 276 and the shaft guide groove 277 may be formed slightly greater than a distance in the circumferential direction which the flow adjusting device 300 rotates. Accordingly, in a process of movement of the first gear 360, the first gear 360 may be prevented from being separated from the first rack 276. In addition, in a process of movement of the first gear shaft 362, the first gear shaft 362 may be prevented from interfering with the end portion of the shaft guide groove 277.

The rotational shaft 354 may be provided on a lower surface portion 351a of the guide main body 351. That is, the rotational shaft 354 may protrude in the downward direction from the lower surface portion 351a. The rotational shaft 354 may be inserted or provided in a shaft insertion portion 284 of the second discharge guide 280, and may be rotated in the shaft insertion portion 284. That is, when the first gear 360 rotates, the first gear shaft 362 and the first gear 360 may rotate about the rotational shaft 354 in the circumferential direction. The rotational shaft 354 may rotate in the shaft inserting portion 284. Accordingly, the flow adjusting device 300 may be rotated in a first direction, that is, in the clockwise direction or in the counterclockwise direction about the longitudinal direction as the axial direction.

The first guide may include bearings 353, and 355 that easily rotate the flow adjusting device 300 in the first direction. The bearings 353, 355 may reduce a friction force generated in the rotational process of the flow adjusting device 300. The bearings 353 and 355 include a first bearing 353 provided on a lower surface of the rotational guide 350. For example, the first bearing 353 may include a ball bearing.

In addition, the first guide may include a bearing supporting portion or support 354 that protrudes in the downward direction from the lower surface portion 351a to support the first bearing 353. The bearing supporting portion 354 may be formed a set or predetermined length, to guide the first bearing 353 to be disposed at a position at which the first bearing 353 is capable of being in contact with the rotational guide plate 283.

The rotational guide plate 283 may include a bearing groove 285, into which the first bearing 353 may be inserted. In a process of rotation of the flow adjusting device 300 in the first direction, the first bearing 353 may be movable with the first bearing being inserted into the bearing groove 285. The first bearing 353 may be rotated along a rotating radius which is set about the rotational shaft 354. That is, the set rotating radius may be referred to as a "second rotating radius". The second rotating radius may be formed to be less than the first rotating radius. That is, a distance from the rotational shaft 354 to the first bearing 353 may be shorter than a distance from the rotational shaft 354 to the first gear shaft 352. According to this configuration, the lower surface portion 351a may be rotated by being stably supported by the third air guide 270 and the second discharge guide 280.

When the first gear shaft 362 is moved along the shaft guide groove 277, the first bearing 353 may be moved along the bearing groove 285. In order to allow the first gear shaft 362 and the first bearing 353 to be smoothly moved, a set curvature of the shaft guide groove 277 and a set curvature of the bearing groove 285 may be equal to each other.

The bearings 353 and 355 may include a second bearing 355. The second bearing 355 may be rotatably installed or provided at the rim portion 351b. A bearing insertion portion 351c, to which the second bearing 355 may be coupled, may be formed at the rim portion 351b. The bearing insertion portion 351c may be depressed in the upward direction from a lower surface of the rim portion 351b. In addition, a plurality of second bearing 355 may be provided. The second bearing 355 may be in contact with the discharge inner wall 282 of the second discharge guide 280, that is, the inner circumferential surface of the discharge inner wall 282 may form a contacting surface of the second bearing 355. The flow adjusting device 300 may be easily rotated in the first direction by the second bearing 355 rotating about the rotational shaft 354 along the inner circumferential surface of the discharge inner wall 282.

The first direction rotation of the flow adjusting device 300 will be briefly described with reference to FIG. 9. If the first gear motor 363 is operated, the first gear 360 may be rotated. When viewed from a top, the first gear motor 363 may be rotated in the clockwise direction or the counterclockwise direction. Accordingly, the first gear 360 may be rotated in the clockwise direction or the counterclockwise direction.

For example, if the first gear motor 363 is rotated in the clockwise direction, the first gear 360 and the first gear shaft 362 may be moved in the counterclockwise direction along the shaft guide groove 277. On the other hand, if the first gear motor 363 is rotated in the counterclockwise direction, the first gear 360 and the first gear shaft 362 may be moved in the clockwise direction along the shaft guide groove 277.

As the first gear 360 is moved in the clockwise direction or in the counterclockwise direction, the flow adjusting device 300 may be rotated in a same direction as a movement direction of the first gear 360. In this process, the first bearing 353 may be moved along the bearing groove 285, and the second bearing 355 may be moved along the inner circumferential surface of the discharge inner wall 282. Accordingly, the flow adjusting device 300 may be stably rotated along a set flow path in the lateral direction.

Figure 11:
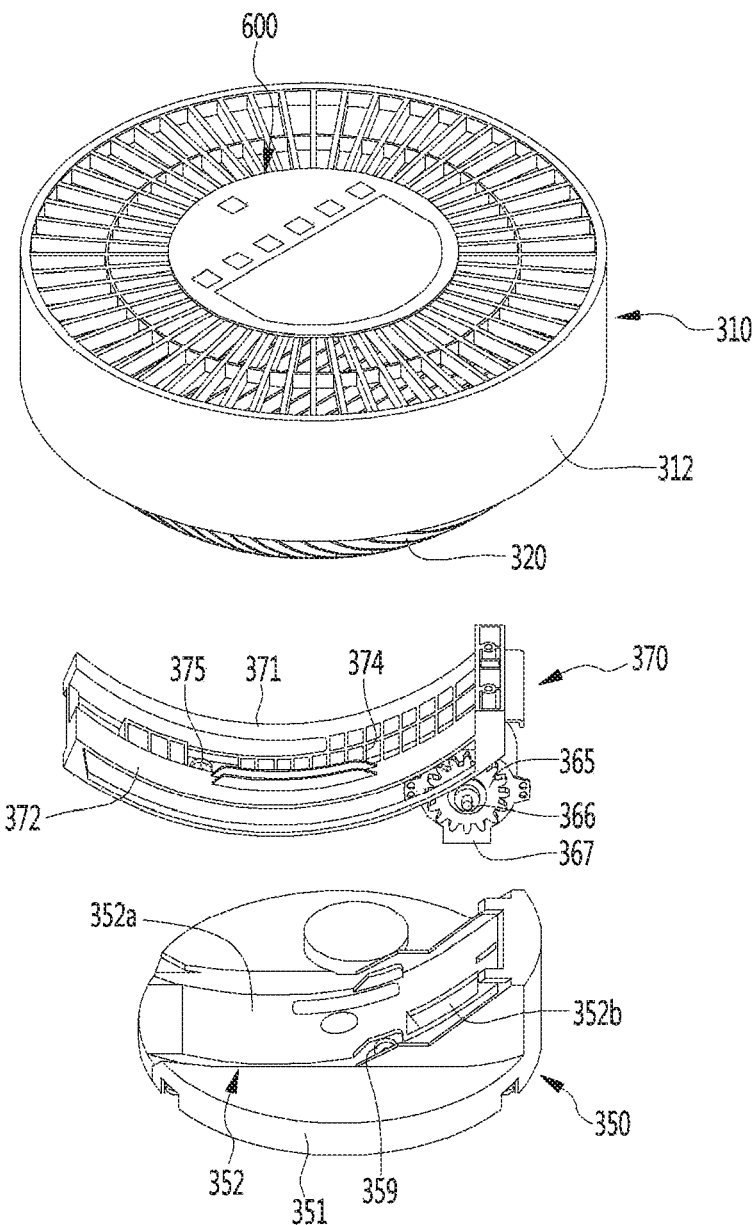
FIG. 11 is an exploded perspective view of the air flow control device according to an embodiment.
Figure 12:
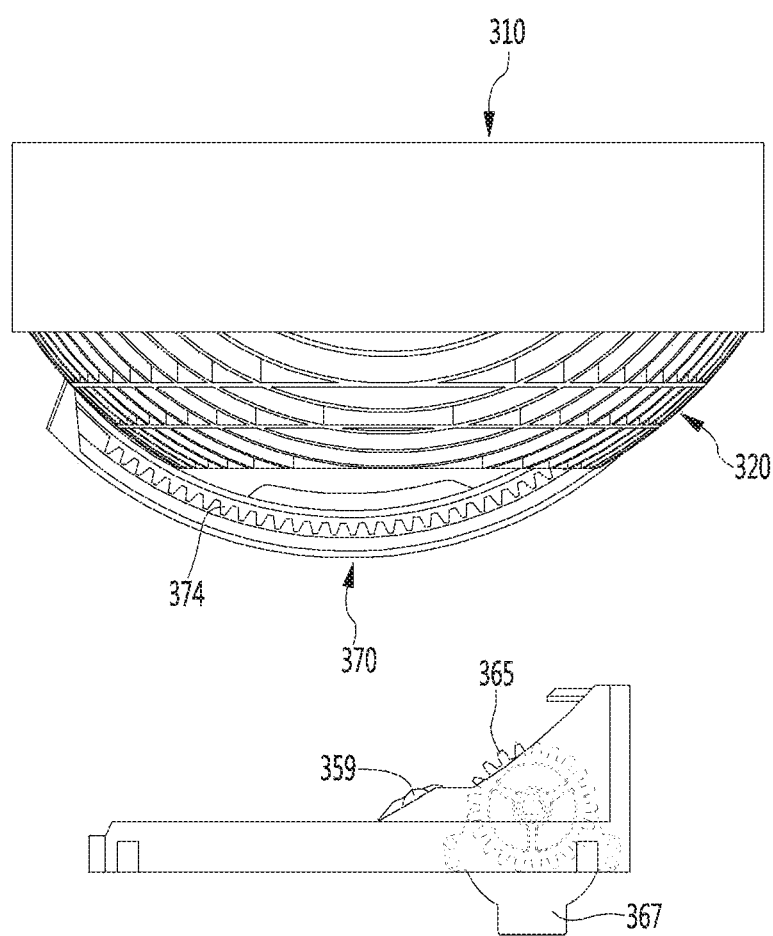
FIG. 12 is an exploded perspective view of a drive portion and a fixing portion of the air flow control device according to an embodiment.
Figure 13:
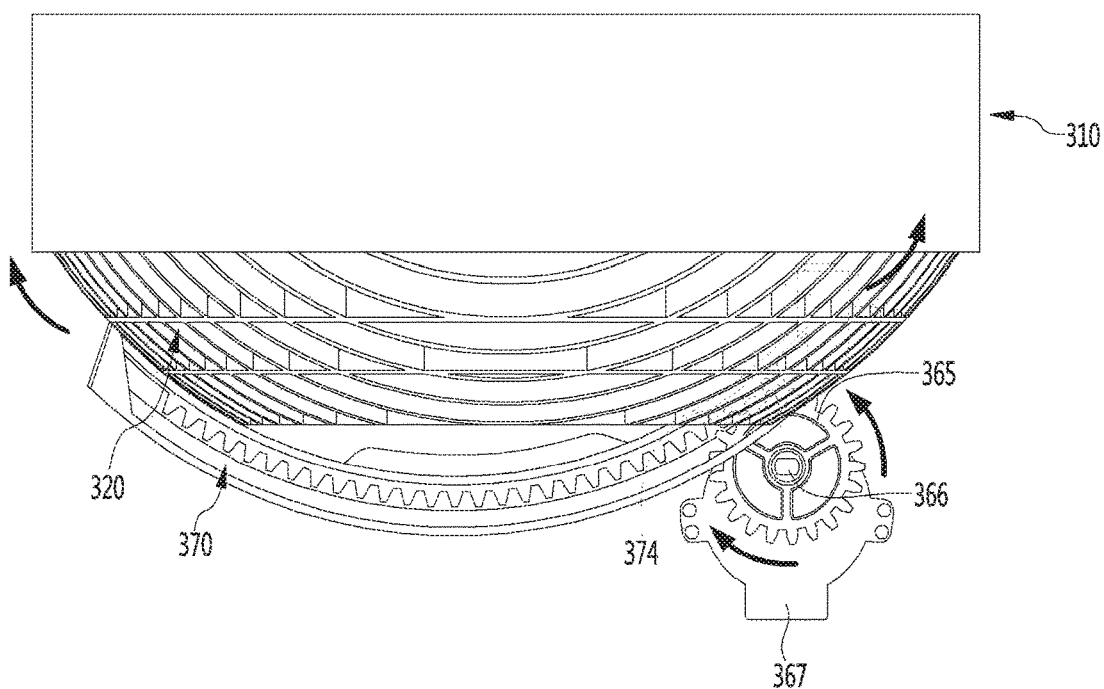
FIG. 13 is a view illustrating a state in which a second rack and a second gear, which are provided in the air flow control device, are interlocked with each other according to an embodiment.

FIG. 11 is an exploded perspective view of the flow adjusting device according to an embodiment. FIG. 12 is an exploded perspective view of a drive portion and a fixing portion of the flow adjusting device according to an embodiment. FIG. 13 is a view illustrating a state in which a second rack and a second gear, which are provided in the flow adjusting device, are interlocked with each other according to an embodiment.

Referring to FIGS. 7, 11, and 12, the flow adjusting device 300 according to an embodiment may include a second guide mechanism or guide that guides rotation in the vertical direction of the flow adjusting device 300. The second guide may include a fixing guide member or guide 352, which may be fixed to the guide main body 351. The rotational shaft 354 may be provided in a lower surface of the fixing guide 352.

The fixing guide 352 may support a lower side of the rotation guide 370, and include a first guide surface 352a, which may guide the second direction rotation of the rotation guide 370. The first guide surface 352a may form at least a portion of an upper surface of the fixing guide 352, and may extend rounded in the upward direction, corresponding to a rotational path of the rotation guide 370.

The fixing guide 352 may further include a first guide bearing 359, which may reduce a friction force generated at a time of rotating movement of the rotation guide 370 by being in contact with the rotation guide 370. The first guide bearing 359 may be positioned to or at a side of the first guide surface 352a.

The fixed guide 352 may further include a second gear inserting portion 352b, into which the second gear 365 may be inserted for rotation of the rotation guide 370. The second gear inserting portion 352b may be formed on or at one side of the first guide surface 352a. For example, the second gear inserting portion 352b may have a shape at least a portion of the first guide surface 352a being cut. The second gear 365 may be positioned to or at a lower side of the first guide surface 352a and at least a portion of the second gear 365 may project to an upper side of the second gear inserting portion 352b through the second gear inserting portion 352b.

The second guide may include a second gear motor 367, which may be coupled to the second gear 365 and provide a drive force. For example, the second gear motor 367 may include a step motor. The second guide may include a second gear shaft 366 that extends from the second gear motor 367 to the second gear 365. When the second gear motor 367 is driven, the second gear shaft 366 and the second gear 365 may be rotated together.

The second guide may further include a rotation guide 370, which may be provided on or at an upper side of the fixing guide 352. The rotation guide 370 may be coupled to a lower side of flow guide 320.

That is, the rotation guide 370 may include a main body portion or body 371, which may be supported by the fixing guide 352. The main body portion 371 may include a second guide surface 372, which may move along the first guide surface 352a. The second guide surface 372 may be rounded corresponding to a curvature of the first guide surface 352a.

The rotation guide 370 may further include a second guide bearing 375, which may reduce a friction force generated at a time of rotating movement of the rotation guide 370 by being in contact with the fixing guide 352. The second guide bearing 375 may be positioned on or at a side of the second guide surface 372.

The rotation guiding 370 may include a second rack 374 linked to the second gear 365. A plurality of gear teeth may be formed in the second gear 365 and the second rack 374, and the second gear 365 and the second rack 374 may be geared to each other through the plurality of gear teeth.

If the second gear motor 367 is driven, the rotation guide 370 rotates in the vertical direction by linkage of the second gear 365 and the second rack 374. Accordingly, the flow adjusting device 300 may perform the second direction rotation according to the movement of the rotation guide 370.

The second direction rotation of the flow adjusting device 300 will be described with reference to FIG. 13.

If the second gear motor 367 is operated, the second gear 365 may be rotated. The second gear motor 367 may be rotated in the clockwise direction or in the counterclockwise direction relative to the radial direction. Accordingly, the second gear 365 may be rotated in the clockwise direction or in the counterclockwise direction.

For example, if the second gear motor 367 is rotated in the clockwise direction, the second gear 365 may be rotated in the clockwise direction, and the second rack 374 rotated in the counterclockwise direction by linkage with the second gear 365. As the second rack 374 is rotated, the rotation guide 370 and the flow guide 320 may be rotated together. Finally, the fan housing 310 may be rotated in the counterclockwise direction.

On the other hand, if the second gear motor 367 is rotated in the counterclockwise direction, the second gear 365 may be rotated in the counterclockwise direction, and the second rack 374 rotated in the clockwise direction by linkage with the second gear 365. As the second rack 374 is rotated, the rotation guide 370 and the flow guide 320 may be rotated together. Finally, the fan housing 310 may be rotated in the clockwise direction. Accordingly, the flow adjusting device 300 may be stably rotated along a set path in the vertical direction.

Figure 14:
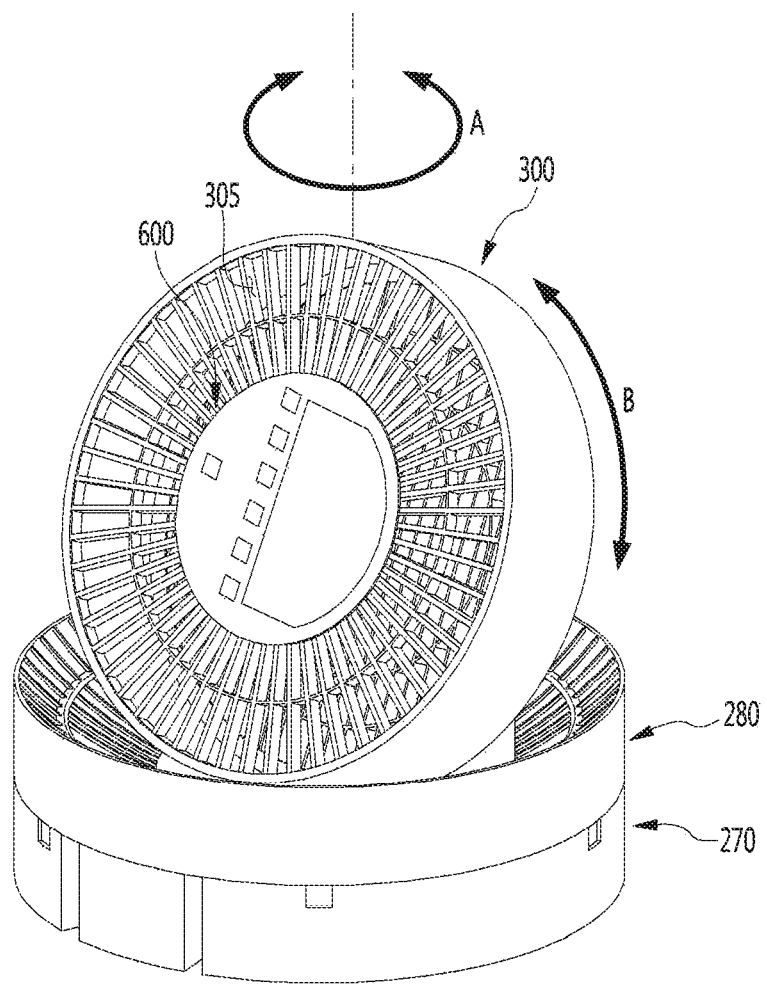
FIGS. 14 and 15 are views illustrating a state in which the air flow control device is located at a second position according to an embodiment.
Figure 15:
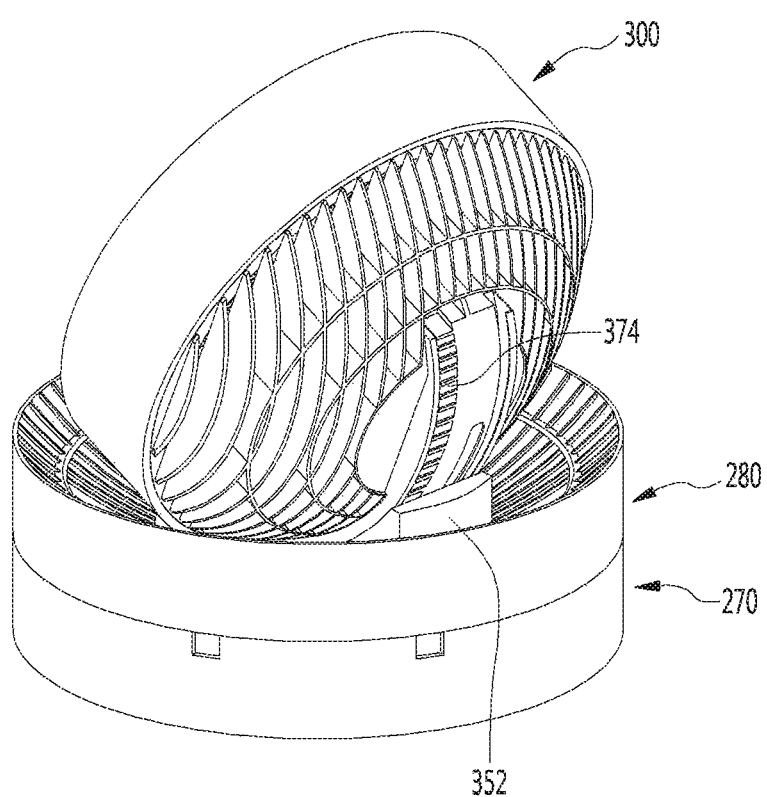
Figure 16:
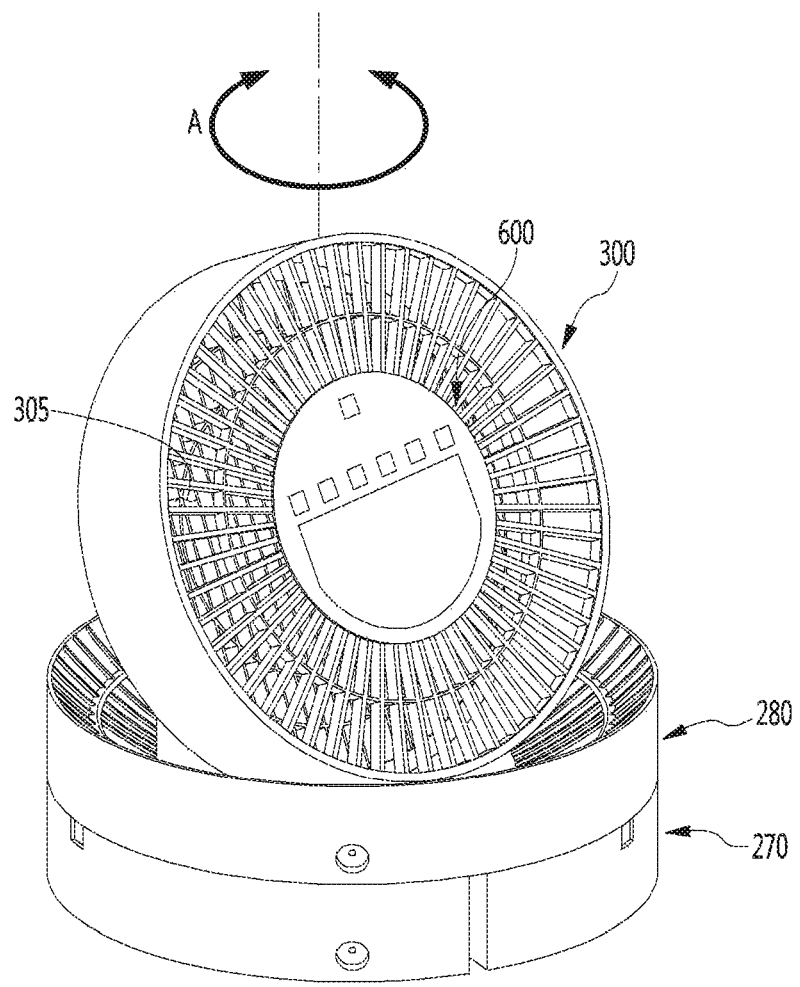
FIG. 16 is a view illustrating a state in which the air flow control device of FIG. 14 is rotated in direction A.

FIGS. 14 and 15 are views illustrating a state in which the flow adjusting device is located at a second position according to an embodiment. FIG. 16 is a view illustrating a state in which the flow adjusting device of FIG. 14 is rotated in direction A.

FIGS. 14 and 15 illustrate a state in which the flow adjusting device 300 protrudes to the upper side of the second discharge guide 280, that is, a state (second position) in which the fan housing 310 is inclined in the upward direction as the rotation guide 370 is rotated in the upward direction. As the flow adjusting device 300 is vertically rotated in a direction "B" shown in FIG. 14, the flow adjusting device 300 may be moved to the first position (see FIG. 1) or the second position. When the flow adjusting device 300 is located at the first position, the introduction grill 325 is disposed on the upper surface of the second discharge grill 288. On the other hand, when the flow adjusting device 300 is located at the second position, the introduction grill 325 is spaced apart from the upper surface of the second discharge grill 288 in the upward direction.

The third fan 330 may be selectively operated based on whether the flow adjusting device 300 is located at the first position or the second position. That is, referring to FIG. 23, the first and second fans 160 and 260 may be rotated to generate air flow in the state in which the flow adjusting device 300 is located at the first position. Air suction and discharging (first flow) at a lower portion of the air cleaner 10 may be generated by operation of the first fan 160. In addition, air suction and discharging (second flow) at an upper portion of the air cleaner 10 may be generated by the operation of the second fan 260. The first flow and the second flow may be separated from each other by the dividing device 400.

In addition, the third fan 330 may be selectively operated. If the third fan 330 is operated, the second flow may be more strongly generated. That is, a strong discharge air current at the upper portion of the air cleaner 10 may be generated by the second fan 260 and the third fan 330, and may be discharged through the second discharge portion 305. The third fan 330 may not be operated.

In the state in which the flow adjusting device 300 is located at the second position, the first and second fans 160 and 260 may be rotated to generate the first flow and the second flow. In addition, the third fan 330 may be operated. The second position is a position in which the airflow control device 300 is inclined by a set or predetermined angle in the upward direction, relative to the first position of the flow adjusting device 300. For example, the set or predetermined angle may be about 60 degrees.

Figure 24:
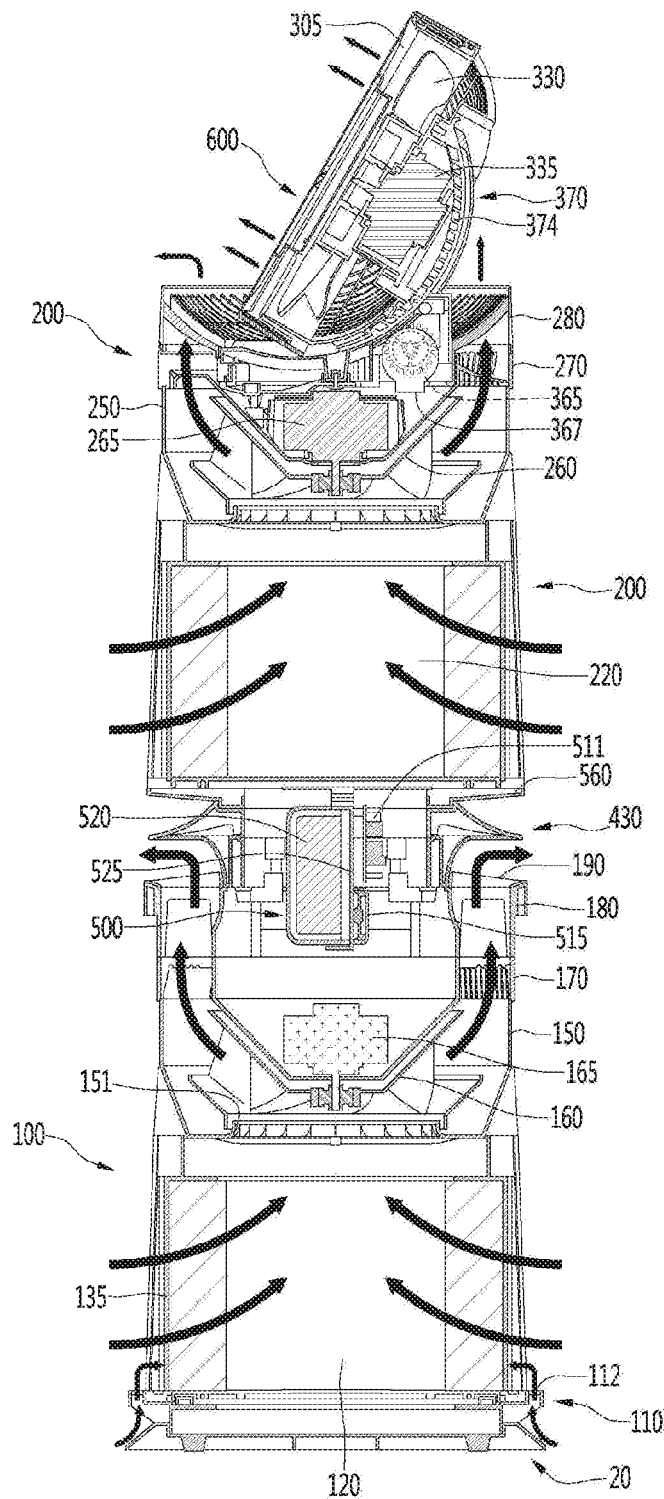

That is, referring to FIG. 24, by the operation of the third fan 330, at least a portion of air which is discharged through the second discharge guide 280 may be introduced to the inside of the third fan housing 310, and may be discharged from the second discharge portion 305 via the third fan 330. Accordingly, purified air may reach a position distant from the air cleaner 10.

In the state in which the flow adjusting device 300 is located at the second position, the flow adjusting device 300 may be rotated in the lateral direction, relative to the side direction. FIG. 14 illustrates a state in which the flow adjusting device 300 is located to face in one direction (left direction relative to FIG. 14) in the state in which the flow adjusting device 30 is located at the second position. The one direction may be a direction which faces at 45 degrees to a left or first side, relative to the front of the air cleaner 10.

The flow adjusting device 300 may be located to face in another direction in the state in which the flow adjusting device 300 is located at the second position. The other direction may be a face which faces at 45 degrees to a right or second side, relative to the front of the air cleaner 10. That is, the rotation angle of the flow adjusting device 300 may be about 90 degrees.

As described above, the flow adjusting device 300 may be rotated in the lateral direction relative to the axial direction, and thus, discharge air current may be blown a long distance in various directions, relative to the air cleaner 10.

Figure 17:
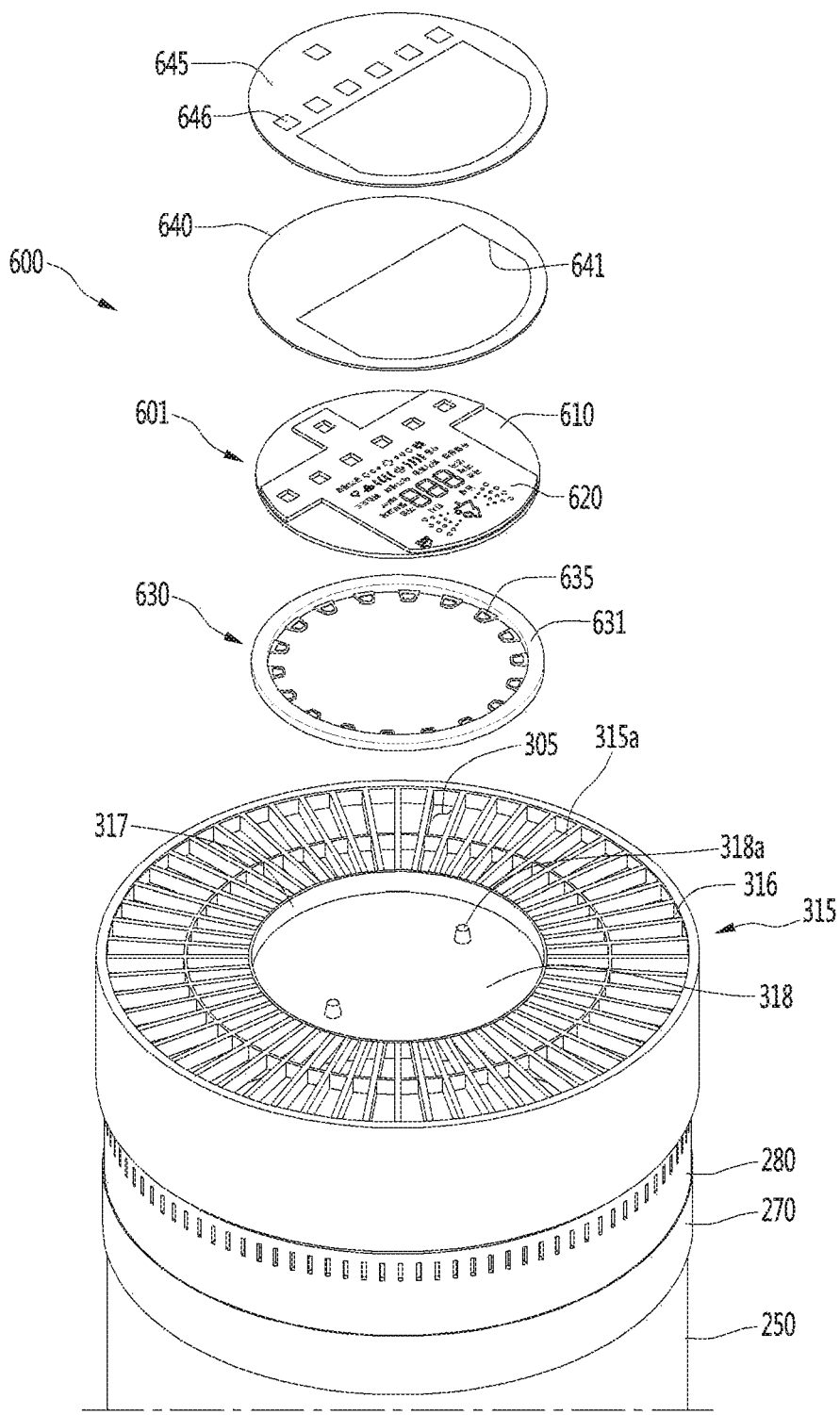
FIG. 17 is an exploded perspective view of a display device which is coupled to a discharge grill according to an embodiment.
Figure 19:
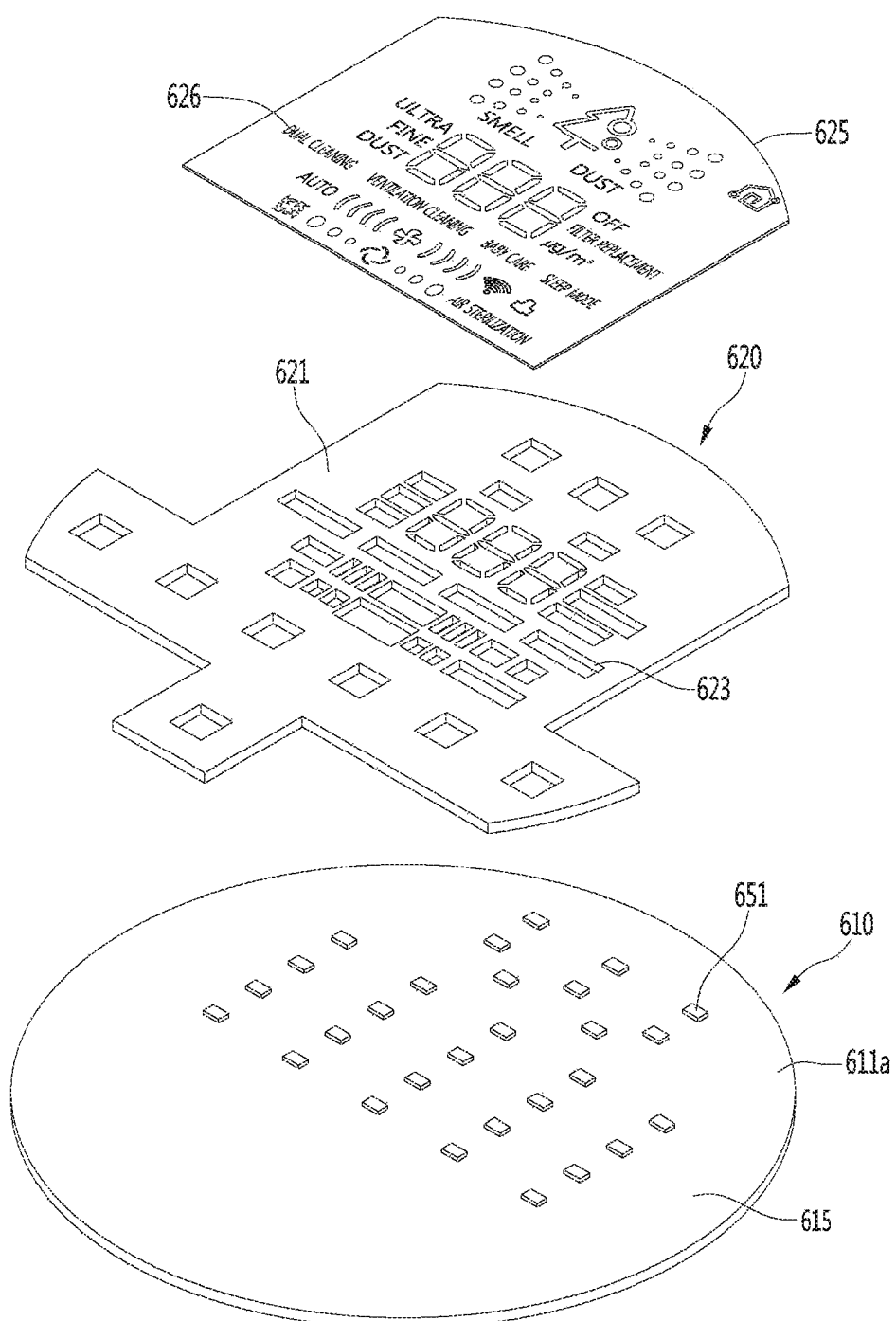
FIG. 19 is an exploded perspective view of the PCB assembly of FIG. 18.
Figure 20:
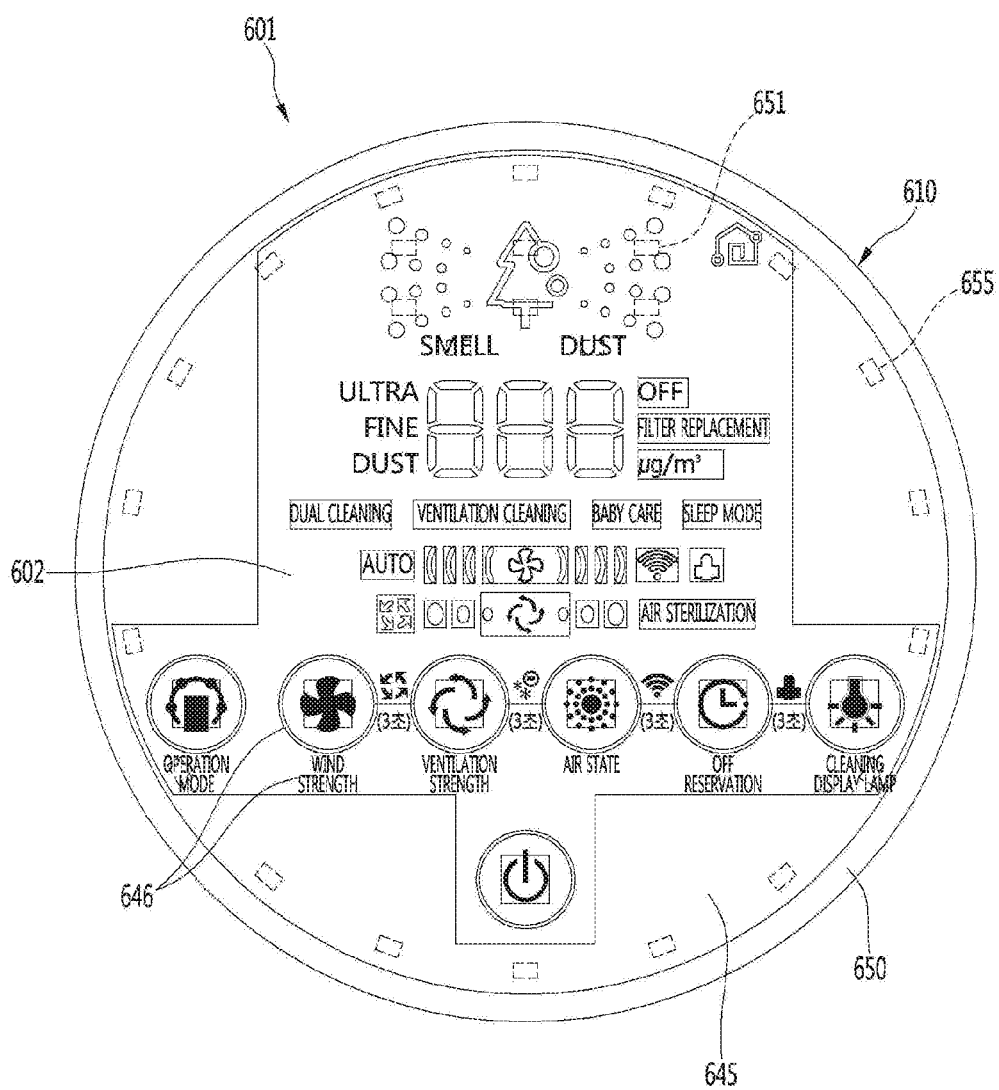
FIG. 20 is a view of an upper surface of a display device according to an embodiment.
Figure 21:
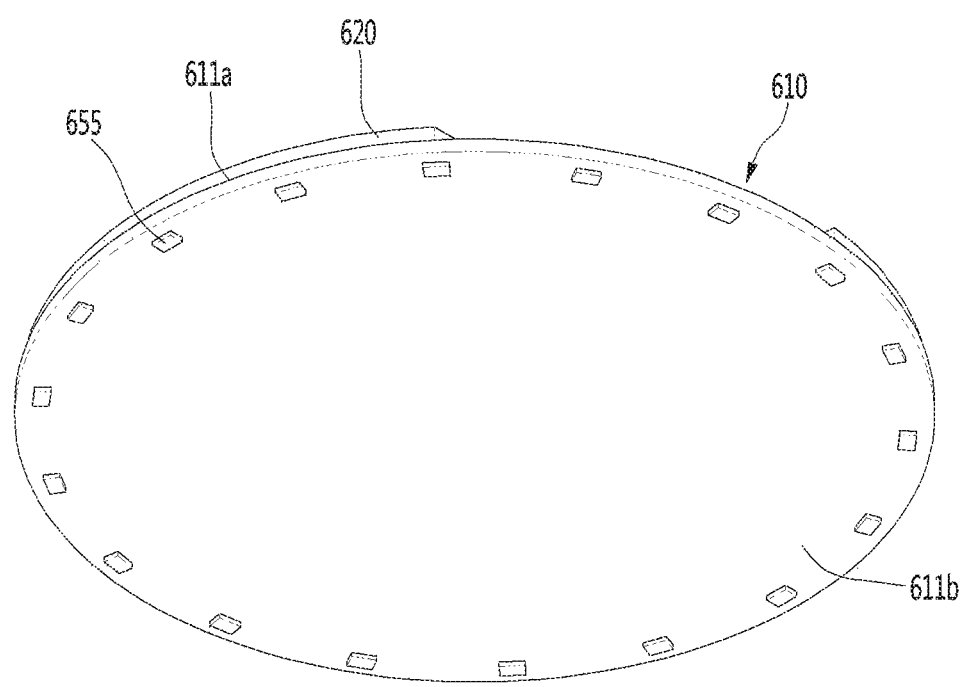
FIG. 21 is a view of a lower surface of the PCB assembly according to an embodiment.

FIG. 17 is an exploded perspective view of the display device which is coupled to the discharge grill according to an embodiment. FIG. 18 is a view illustrating a state in which a PCB assembly is coupled to the discharge grill according to an embodiment. FIG. 19 is an exploded perspective view of the PCB assembly of FIG. 18. FIG. 20 is a view of an upper surface of a display device according to an embodiment. FIG. 21 is a view of a lower surface of the PCB assembly according to an embodiment.

Referring to FIGS. 17 to 21, the display device 600 according to this embodiment may be installed or provided at an upper portion of the air cleaner 10. The display screen 602 of the display device 600 may form at least a portion of the upper surface of the air cleaner 10.

The display device 600 may be installed or provided in or on the discharge grill 315. The depression portion 318, which may be a depressed in the downward direction may be provided at a substantially center portion of the discharge grill 315, and the plurality of grill portions 315a may extend toward the outside in the radial direction from the depression portion 318. In addition, the display device 600 may be disposed or provided on or at an upper side of the depression portion 318.

The display device 600 may include the PCB assembly 601. The PCB assembly 601 may include the display PCB 610 on which a plurality of illumination sources 651 and 655 may be provided, and a reflector 620, which may be coupled to an upper side of the display PCB 610 to allow light irradiated from the plurality of illumination sources 651 to be concentrated toward the display screen 602.

The plurality of illumination sources 651 and 655 may include a first illumination source 651 that displays operation information of the air cleaner 10 and a second illumination source 655 that displays a rim portion or rim of the display screen 602 of the display device 600. The display screen 602 may be a set or predetermined area (hereinafter, referred to as a "display area") in which the information may be displayed, and may be formed on an upper surface of the display device 600. In addition, the rim or portion of the display screen 602 may form a boundary of the display area.

The display PCB 610 may include a board main body 611, which may have a substantially circular shape. The board main body 611 may include a main body front surface portion or surface 611*a*, on which the first illumination source 651 may be installed or provided, and a main body rear surface portion or surface 611*b*, on which the second illumination source 655 may be installed or provided.

A plurality of first illumination sources 651 may be provided on the main body front surface portion 611*a*, corresponding to a shape of a displayed content. In addition, a plurality of second illumination sources 655 may be provided. The plurality of second illumination sources 655 may be arranged along a rim portion or rim of the main body rear surface portion 611*b*. For example, the plurality of second illumination sources 655 may be arranged in a circular shape.

The reflector 620 may include a reflector main body 621 and a through hole 623, which may be formed in the reflector main body 621 and allow light irradiated from the first illumination source 651 to be concentrated in the upward direction. The reflector main body 621 may be made of an opaque material through which transmission of light may be limited, or an opaque material may be coated on the reflector main body 621.

A reflector film 625 may be provided on or at an upper side of the reflector 620. The reflector film 625 may include a pattern display portion display 626 at or on which a content of displayed information, that is, a predetermined character, number, or symbol, may be displayed. The light concentrated through the reflector 620 may act on the pattern display portion 626, thereby implementing predetermined information. The pattern display portion 625 may be made of a transparent material. For example, as shown in FIG. 19, the pattern display portion 626 may include characters conveying information to a user, such as "smell," "dust," "fine dust," and "filter replacement," a pattern 888 capable of displaying numbers, and/or a symbol that represents a strength of a blowing amount, for example.

The first illumination source 651 may be disposed or provided at a position corresponding to the pattern display portion 626. For example, the first illumination source 651 may be disposed or provided on or at a lower side of the pattern display portion 626. As a plurality of pattern display portions 626 may be provided to implement various patterns, a plurality of first illumination sources 651 may be provided corresponding to the plurality of pattern display portions 626. Light irradiated from the first illumination source 651 may be exposed to the outside by passing through the pattern display portion 626. In addition, various information may be displayed by on/off control of the plurality of first illumination sources 651.

The display device 600 may include the diffusing plate 630, which may surround an outside of the PCB assembly 601. The diffusing plate 630 may be a component that forms the rim portion or rim 650 of the display screen 602 by diffusing light irradiated from the second illumination source 655.

The diffusing plate 630 may be disposed or provided along the rim portion of the depression portion 318. That is, the diffusing plate 630 may include a plate main body 631, which may surround the display PCB 610 and an illumination accommodating portion 635, which may protrude from an inner circumferential surface of the plate main body 631 to allow the second illumination source 655 to be accommodated therein. The plate main body 631 may have a ring shape, and may be supported by the discharge grill 315. In addition, the plate main body 631 and the illumination accommodating portion 635 may be integrally formed.

The plate main body 631 and the illumination accommodating portion 635 may be made of a translucent material which is capable of refracting or diffusing light. For example, the plate main body 631 and the illumination accommodating portion 635 may be made of an acrylic material.

The plate main body 631 may form the rim portion 650 of the display screen 602. That is, an upper portion of the plate main body 631 may be exposed to the upper surface of the air cleaner 10, and light irradiated from the second illumination source 655 may be diffused through the illumination accommodating portion 635 and the plate main body 631. In addition, the diffused light may move to the upper portion of the air cleaner 10, thereby forming the rim portion 650.

As the plate main body 631 and the illumination accommodating portion 635 are made of a translucent material, the rim portion 650 may be implemented using soft light. Thus, a display screen having a comfortable feeling may be implemented.

The display device 600 may further include a display cover 640, which may be provided on or at an upper side of the PCB assembly 601. The display cover 640 may be understood as a component that supports the outside of the display PCB 610 and maintains a cover film 645 flat. The display cover 640 may be made of an opaque material to prevent transmission of light.

A cover hole 641, which may have a shape corresponding to the reflector film 625, may be formed in the display cover 640. According to the configuration of the cover hole 641, although the display cover 640 is coupled to the reflector 620, the reflector film 625 may be exposed in the upward direction.

The cover film 645 may be provided on or at an upper side of the display cover 640. For example, the cover film 645 may be attached to an upper surface of the display cover 640. The cover film 645 may be made of a translucent material to allow a portion of light transferred from the PCB assembly 601 to be transmitted therethrough. For example, the translucent material may include an acrylic or polymethyl methacrylate (PMMA)resin. The cover film 645 may be provided, so that information displayed through the display device 600 may be prevented from being extremely dazzling. The cover film 645 may include a film display portion or display 646, which may allow a user to input a predetermined command or display a portion of a plurality of operation information of the air cleaner 10.

Figure 22:
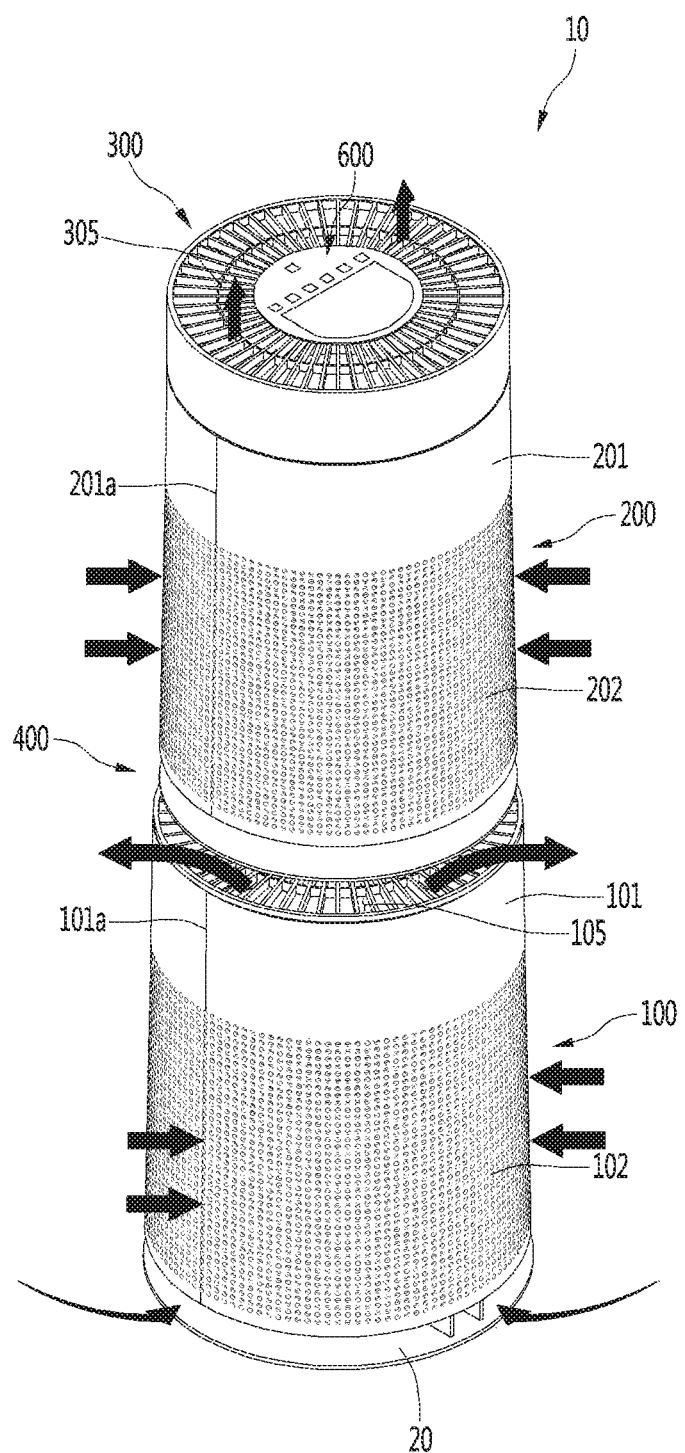
FIGS. 22 to 24 are views illustrating a state in which air flows in the air cleaner of FIG. 1.
Figure 23:
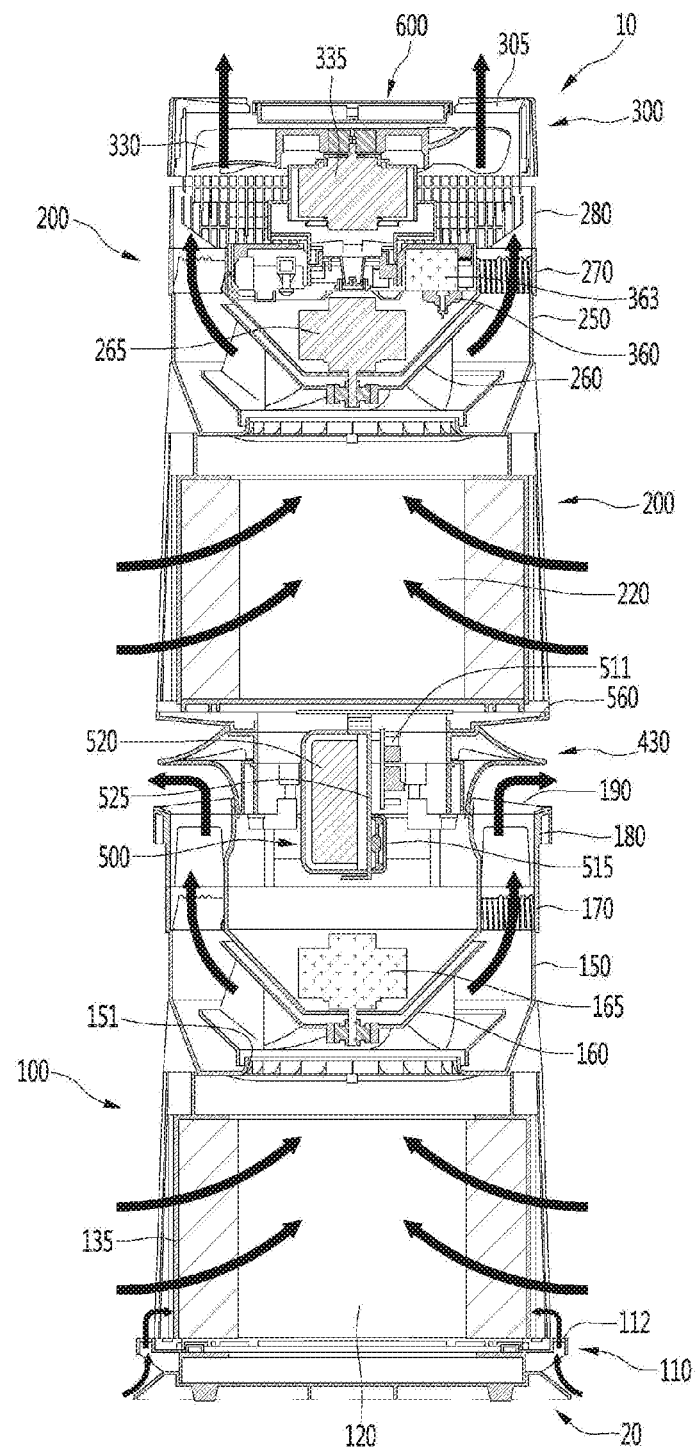

FIGS. 22 to 24 are views illustrating a state in which air flows in the air cleaner of FIG. 1.

First, the flow of air according to driving of the first blowing device 100 will be described. If the first fan 160 is driven, indoor air may be suctioned inside of the first case 101 through the first suction portion 102 and the base suction portion 103. The suctioned air may pass through the first filter 120, and foreign materials in the air may be filtered in this process. In a process in which air passes through the first filter 120, the air may be suctioned in the radial direction of the first filter 120, filtered, and then flow in the upward direction.

The air having passed through the first filter 120 may flow to the upper side in the radial direction while passing through the first fan 160 and stably flow in the upward direction while passing through the first air guide 170 and the second air guide 180. Air passing through the first air guide 170 and the second air guide 180 may pass by the first discharge guide 190 and flow in the upward direction through the first discharge portion 105. Air which is discharged through the first discharge portion 105 may be guided by the dividing plate 430 positioned at the upper side of the first discharge guide 190, and thus, may be discharged outside of the air cleaner 10.

If the second fan 260 is driven, indoor air may be suctioned inside of the second case 201 through the second suction portion 202 and the base suction portion 103. The suctioned air may pass through the second filter 220, and foreign materials in air may be filtered in this process. In a process in which air passes through the second filter 220, the air may be suctioned in the radial direction of the second filter 220, filtered, and then flow in the upward direction.

Air which passes through the second filter 220 may flow to the upper side in the radial direction while passing through the second fan 160, and stably flow in the upward direction while passing through the third air guide 270 and the second discharge guide 280. Air having passed through the third air guide 270 and the second discharge guide 280 may be discharged through the second discharge portion 305 via the flow adjusting device 300.

The flow adjusting device 300 may be rotated provided in the vertical direction by the second guide. For example, as shown in FIGS. 22 to 24, if the flow adjusting device 300 is located at or in the first position, air which is discharged from the flow adjusting device 300 may flow in the upward direction. On the other hand, if the flow adjusting device 300 is located at or in the second position, air which is discharged from the flow adjusting device 300 may flow toward the front upper side. By the flow adjusting device 300, an air volume of air which is discharged from the air cleaner 10 may be increased, and purified air may be supplied to a position distant from the air cleaner 10.

That is, if the third fan 330 of the flow adjusting device 300 is driven, at least a portion of air which is discharged from the second discharge guide 280 may be introduced to the inside of the third fan housing 310. Then, the introduced air may pass through the third fan 330, and may be discharged to the outside through the second discharge portion 305.

The flow adjusting device 300 may be rotated in the lateral direction by the first guide in the state in which the flow adjusting device 300 is located at the second position. For example, as shown in FIGS. 14 and 15, when the flow adjusting device 300 faces the front upper side, air which is discharged through the second discharge portion 305 may flow toward the front upper side. On the other hand, as shown in FIG. 16, when the flow adjusting device 300 faces the rear upper side, air which is discharged through the second discharge portion 305 may flow toward the rear upper side.

According to this action, air which is discharged from the air cleaner 10 does not simply flow in the upward direction, but rather, may flow in the frontward direction, and thus, an air current toward a space relatively distant from the air cleaner 10 may be generated. As the separate third fan 330 is provided in the flow adjusting device 300, a blowing force of the discharged air may be increased.

In addition, the flow adjusting device 300 is capable of performing the first direction rotation, and thus, air may be discharged to both sides of the front of the air cleaner 10. Accordingly, an air current may be provided toward a relatively wide room space.

The flow adjusting device 300 may be selectively operated based on an operation mode of the air cleaner 10. When the air cleaner 10 is operated in a general operation mode (first operation mode), the flow adjusting device 300 may be located at or in the first position in which the flow adjusting device 300 is laid out, as shown in FIGS. 22 and 23. Then, the first and second blowing devices 100 and 200 may be driven, thereby forming a plurality of independent air currents.

That is, if the first blowing device 100 is driven, air may be suctioned through the first suction portion 102 and the base suction portion 103 and then discharged through the first discharge portion 105 by passing through the first filter 120 and the first fan 160. In addition, if the second blowing device 200 is driven, air may be suctioned through the second suction portion 202 and pass through the third fan 330 via the second filter 220 and the second fan 260. The third fan 330 may be driven to have a rotation number corresponding to a rotation number of the second fan 260, thereby guiding air flow. The air current may be directed toward both sides of the front of the air cleaner while the flow adjusting device 300 is performing the first direction rotation in the state in which the flow adjusting device 300 is located at the first position.

On the other hand, when the air cleaner 10 is operated in a flow conversion mode (second operation mode), the flow adjusting device 300 may protrude from the upper end portion of the air cleaner 10 by being rotated in the upward direction, as shown in FIG. 24. In the flow conversion mode, driving of the first and second blowing devices 100 and 200 may be identical to driving of the first and second blowing devices 100 and 200 in the general operation mode.

Then, the third fan 330 may be driven, and accordingly, at least a portion of air having passed through the second fan 260 and the discharge flow path 282a of the second discharge guide 280 may be introduced to the third fan housing 310. In addition, at least a portion of the introduced air may be discharged toward the front upper side or the rear upper side of the air cleaner 10 while passing through the third fan 330.

According to embodiments disclosed herein, a suction capacity may be improved as the suction portion is formed along an outer circumferential surface of a cylindrical case and a structural resistance of the case may not be generated in an air suction process. In addition, discharge of air in the upward direction may be guided through the second blowing device and discharge of air in the frontward direction may be guided by the flow adjusting device, which may be provided on or at an upper side of the second blowing device. Discharge of air in the lateral direction may be guided, in a process of rotating of the flow adjusting device. Finally, an air cleaning function of an indoor space may be improved as discharge of air in various directions may be guided relative to the air cleaner and a discharge air flow may be formed to extend a long distance from the air cleaner. A discharge air flow may be easily generated toward a circumferential space of a person in a room whether the person in the room sitting down or standing up.

In addition, as the flow adjusting device may include a first guide mechanism or guide which guides rotation in a lateral direction and a second guide mechanism or guide which guides rotation in vertical direction, the air flow control device may control a discharge air current while being rotated in the lateral direction by operation of the first guide mechanism in a state in which the air flow control device is located at a first position at which the air flow control device is laid out by the operation of the second guide mechanism or a second position at which the air flow control device is erected or at an inclined by the operation of the second guide mechanism. In addition, as a third fan may be provided in the air flow control device, air may be discharged by adding a flow force generated by the third fan to air which flows through the second blowing device. Thus, a strong discharge air current is capable of being generated, so that an air current may reach a position distant from the air cleaner.

As each of the first guide mechanism and the second guide mechanism includes a gear motor and a gear, rotation in the vertical direction or the lateral direction of the air flow control device may be easily performed. Further, a display device or device may be provided at an upper portion of the air flow control device, so that operation information of the air cleaner may be easily recognized at the outside. In particular, the display device may be exposed to the outside not only when the air flow control device is in an inclinedly erected state (second position) relative to an axial direction, but also when the air flow control device is in a laid out state (first position) relative to the axial direction, so that operation information of the air cleaner may be easily identified.

The air flow control device may include a discharge grill, and a depression portion provided at a center portion of the discharge grill. Thus, the display device may be installed, and a discharge portion through which air may be discharged may be formed along a circumference of the depression portion. Accordingly, it is possible to improve a spatial utilization of the air cleaner. Further, it is possible to prevent flow of air discharged through the discharge portion from interfering by the display device.

The display device may include a PCB assembly, that is, a display PCB having a first illumination source and a reflector which may be coupled to the display PCB, so that it is possible to easily implement various characters, numbers, or symbols relative to the operation of the air cleaner. A second illumination source may be provided on a lower surface of the display PCB, and a diffusing plate having an illumination accommodating portion which accommodates the illumination source therein may be provided on a lower side of the display PCB, so that light irradiated from the illumination source may be refracted through the diffusing plate to be easily moved to a rim portion of a front surface of the display device. Finally, it is possible to obtain an effect that information displayed through the display device may be visually emphasized. Accordingly, a user may easily identify information even in a slightly distant distance.

Further, a blowing capacity of the air cleaner may be improved as a plurality of blowing devices may be provided. The air which flows in the radial direction through a centrifugal fan may be easily guided toward the discharge portion in the upward direction, as the centrifugal fan for increasing the blowing capacity of the air cleaner and the air guide device or guide which may be disposed or provided on or at an outlet side of the centrifugal fan may be provided.

Phenomena that interference between the air flows may be prevented as the air flows which are independent from each other may be generated through the first blowing device and the second blowing device. Accordingly, the air flowing capacity may be improved.

Embodiments disclosed herein provide an air cleaner which is capable improving a suction capacity of air which is suctioned to the air cleaner. Embodiments disclosed herein further provide an air cleaner which is capable of sufficiently suctioning air around a person in a room whether the person in the room sitting down or standing up by including a suction flow path which is directed from a circumferential direction of the air cleaner to an inside portion thereof and a suction flow path through which air is introduced through an upper portion and a lower portion of the air cleaner.

Embodiments disclosed herein also provide an air cleaner which is capable of discharging air which is discharged from the air cleaner in various directions and sending the discharged air a long distance. In particular, embodiment disclosed herein provide an air cleaner which is capable of easily discharging air toward a surrounding space of a person in a room whether the person in the room sitting down or standing up by a discharge air flow being easily generated in an upward direction, a frontward direction, and lateral direction of the air cleaner.

Embodiments disclosed herein provide an air cleaner which includes a display device or display capable of easily displaying operation information of the air cleaner to the outside. Embodiments disclosed herein also provide an air cleaner in which the display device may be provided in a rotatable air flow control device, so that a user may easily identify operation information of the air cleaner regardless of a position to which the air flow control device is rotated.

Embodiments disclosed herein provide an air cleaner a blowing capacity of which may be increased. Embodiments disclosed herein further provide an air cleaner in which an air guide device or guide is provide which allows air passing through a centrifugal fan to easily flow toward a discharge portion in an upward direction in a case of adopting the centrifugal fan in order to increase a blowing capacity. Embodiments disclosed herein also provide an air cleaner which improves purification capacity of a filter and in which replacement of the filter is easily performed.

Embodiments disclosed herein additionally provide an air cleaner in which a filter may be easily installed or provided without an installation space for installing the filter in an inside portion of the air cleaner being additionally provided.

Embodiments disclosed herein provide an air cleaner that may include an air cleaning module that includes a main fan to generate an air flow and a filter member or filter to purify air; and an air flow control device or controller movably provided in or at one side of the air cleaning module. The air flow control device may include a sub-fan to control a direction of air flow passing through the air cleaning module. When the air flow control device is in a first location, in a case in which the sub-fan is driven, air may be discharged in an upward direction from the air flow control device. When the air flow control device is in a second location, in a case in which the sub-fan is driven, air may be discharged in a front upward direction from the air flow control device.

The air flow control device may include a guide device or guide to guide a first directional rotation or a second directional rotation of the air flow control device. The first directional rotation may be a rotation of a clockwise direction or a counterclockwise direction, with respect to an axial direction. The second directional rotation may be a rotation of upper or lower direction.

The guide device may include a first guide device to guide the first directional rotation. The air cleaner may further include a third air guide device disposed in an outlet side of the main fan and having a first air flow path. The third air guide device may include an outer wall configured to form an outer circumference surface of the third air guide device, and an inner wall configured disposed in an inner side of the outer wall, the inner wall being configured to form an inner circumference surface of the third air guide device. The first air flow path may be formed between an inner circumference surface of the outer wall and an outer circumference surface of the inner wall.

The first guide device may include a first gear motor which is able to rotate in both directions, and a first gear configured to be connected to the first gear motor to rotate and to have a first gear shaft. The third air guide device may include a first rack which is interlocked with the first gear and extends in a rounded shape in a circumferential direction.

The first guide device may further include a rotating shaft which forms a center of the first direction rotation of the air flow control device. The first gear may rotate with a radius of rotation set around the rotating shaft.

The air cleaning may further include a second discharge guide device or guide disposed or provided in the outlet side of the third air guide device, the second discharge guide device being configured to form a discharging flow path through which the air passing through the first air flow path may flow.

The second discharge guide device may include a discharge outer wall configured to form an outer circumference surface of the second discharge guide device, and a discharge inner wall disposed or provided in or at an inner side of the discharge outer wall, the discharging inner wall being configured to form an inner circumference surface of the second discharge guide device. The discharge flow path may be formed between the inner circumference surface of the discharge outer wall and the outer circumference surface of the discharge inner wall.

The first guide device may include a bearing to guide a first direction rotation of the air flow control device. The bearing may include a first bearing which moves along a bearing groove of the second discharging guide device, and a second be discharging guide bearing which moves along an inner circumferential surface of the second discharging guide device. The guide device may include a second guide device or guide to guide the second direction rotation.

The second guide device may include a second gear motor which is rotatable in both directions, and a second gear which is connected to the second gear motor to rotate. The second guide device may include a rotation guide member configured to be rotatable in upward and downward directions, and a fixed guide member including having a first guide surface to support a lower side of the rotation guide member.

The fixed guide member may further include a first guide bearing contacted with the rotation guide member to reduce a friction occurred when the rotation guide member rotates. The fixed guide member further may include a second gear insertion part to which the second gear inserts. The second gear may extend upward from the first guide surface, passing through the second gear insertion part.

The first location may be where a top of the air flow control device is disposed vertically with respect to an axial direction. The second location may be where the top of the air flow control device is disposed with a slope or incline with respect to the axial direction.

The air flow control device may include a display device or display to display operation information.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air cleaner, comprising:
   a first fan;
   a discharge guide that discharges air passing through the first fan, the discharge guide including a discharge grill having a concave shape in a downward direction; and
   an air flow controller configured to adjust a direction of air discharged from the discharge guide and being movable, the air flow controller including an introduction grill into which the air discharged from the discharge guide is introduced and having a convex shape in the downward direction, wherein:
   when the air flow controller is in a first position of a laid-out state, the introduction grill is seated on an upper surface of the discharge grill, and
   when the air flow controller moves from the first position to a second position of an inclined erected state, the introduction grill is spaced apart from the upper surface of the discharge grill.

2. The air cleaner according to claim 1, wherein the air flow controller slidably moves from the first position to the second position.

3. The air cleaner according to claim 2, wherein the air flow controller includes:
   a fixed guide provided at a lower side of the introduction grill, the fixed guide having a first guide surface which is rounded; and
   a rotation guide having a second guide surface which moves along the first guide surface.

4. The air cleaner according to claim 3, wherein the fixed guide further includes a first guide bearing provided at a side of the first guide surface, the first guide bearing being configured to contact the rotation guide.

5. The air cleaner according to claim 3, further including:
   a gear that communicates with the rotation guide; and
   a gear recess provided at the fixed guide into which the gear is inserted.

6. The air cleaner according to claim 5, wherein the gear is positioned at the first guide surface, and at least a portion of the gear projects upward from the gear recess.

7. The air cleaner according to claim 5, wherein the rotation guide further includes a rack that communicates with the gear.

8. The air cleaner according to claim 3, wherein the rotation guide further includes a second guide bearing provided at a side of the first guide surface, the second guide bearing being configured to move along the first guide surface.

9. The air cleaner according to claim 1, wherein the air flow controller further includes a rotational shaft, and wherein the rotational shaft guides rotation of the air flow controller in a clockwise or counter-clockwise direction when the air flow controller is in the first position or the second position.

10. The air cleaner according to claim 1, wherein the air flow controller further includes a second fan, and wherein the first and the second fans are positioned on a same axis in a longitudinal direction.

11. An air cleaner, comprising:
a first fan;
a discharge guide that discharges air passing through the first fan, the discharge guide including a discharge grill having a concave shape in a downward direction; and
an air flow controller configured to adjust a direction of air discharged from the discharge guide and being movable, the air flow controller including an introduction grill into which the air discharged from the discharge guide is introduced and having a convex shape in the downward direction, wherein:
when the air flow controller is in a first position, the introduction grill is seated on an upper surface of the discharge grill, and
when the air flow controller moves from the first position to a second position, the introduction grill is spaced apart from the upper surface of the discharge grill, and wherein the air flow controller slidably moves from the first position to the second position.

12. The air cleaner according to claim 11, wherein the air flow controller further includes a rotational shaft, and wherein the rotational shaft guides rotation of the air flow controller in a clockwise or counter-clockwise direction when the air flow controller is in the first position or the second position.

13. The air cleaner according to claim 11, wherein the air flow controller further includes a second fan, and wherein the first and the second fans are positioned on a same axis in a longitudinal direction.

14. An air cleaner, comprising:
a first fan;
a discharge guide that discharges air passing through the first fan, the discharge guide including a discharge grill having a concave shape in a downward direction; and
an air flow controller configured to adjust a direction of air discharged from the discharge guide and being movable, the air flow controller including an introduction grill into which the air discharged from the discharge guide is introduced and having a convex shape in the downward direction, wherein:
when the air flow controller is in a first position, the introduction grill is seated on an upper surface of the discharge grill, and
when the air flow controller moves from the first position to a second position, the introduction grill is spaced apart from the upper surface of the discharge grill, and wherein the air flow controller includes:
a fixed guide provided at a lower side of the introduction grill, the fixed guide having a first guide surface which is rounded; and
a rotation guide having a second guide surface which moves along the first guide surface.

15. The air cleaner according to claim 14, wherein the fixed guide further includes a first guide bearing provided at a side of the first guide surface, the first guide bearing being configured to contact the rotation guide.

16. The air cleaner according to claim 15, wherein the rotation guide further includes a second guide bearing provided at a side of the first guide surface, the second guide bearing being configured to move along the first guide surface, and wherein the rotation guide further includes a rack that communicates with the gear.

17. The air cleaner according to claim 14, further including:
a gear that communicates with the rotation guide; and
a gear recess provided at the fixed guide into which the gear is inserted.

18. The air cleaner according to claim 17, wherein the gear is positioned at the first guide surface, and at least a portion of the gear projects upward from the gear recess.

19. The air cleaner according to claim 14, wherein the air flow controller further includes a rotational shaft, and wherein the rotational shaft guides rotation of the air flow controller in a clockwise or counter-clockwise direction when the air flow controller is in the first position or the second position.

20. The air cleaner according to claim 14, wherein the air flow controller further includes a second fan, and wherein the first and the second fans are positioned on a same axis in a longitudinal direction.

* * * * *